United States Patent
Cerezo-Galvez et al.

(10) Patent No.: US 9,688,681 B2
(45) Date of Patent: Jun. 27, 2017

(54) HETEROCYCLIC COMPOUNDS AS PEST CONTROL AGENTS

(71) Applicant: BAYER CROPSCIENCE AKTIENGESELLSCHAFT, Monheim am Rhein (DE)

(72) Inventors: Silvia Cerezo-Galvez, Langenfeld (DE); Thomas Bretschneider, Lohmar (DE); Reiner Fischer, Monheim (DE); Martin Fuesslein, Duesseldorf (DE); Christoph Grondal, Cologne (DE); Peter Jeschke, Bergisch Gladbach (DE); Peter Reinisch, Langenfeld (DE); Mehmet Gueclue, Cologne (DE); Kerstin Ilg, Cologne (DE); Peter Loesel, Leverkusen (DE); Olga Malsam, Roesrath (DE); Arnd Voerste, Cologne (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 14/892,657

(22) PCT Filed: May 23, 2014

(86) PCT No.: PCT/EP2014/060596
§ 371 (c)(1),
(2) Date: Nov. 20, 2015

(87) PCT Pub. No.: WO2014/191301
PCT Pub. Date: Dec. 4, 2014

(65) Prior Publication Data
US 2016/0122353 A1   May 5, 2016

(30) Foreign Application Priority Data

May 28, 2013   (EP) .................................... 13169415

(51) Int. Cl.
| | | |
|---|---|---|
| A61K 31/519 | (2006.01) | |
| C07D 487/04 | (2006.01) | |
| A01N 43/90 | (2006.01) | |

(52) U.S. Cl.
CPC ........... *C07D 487/04* (2013.01); *A01N 43/90* (2013.01)

(58) Field of Classification Search
CPC .................................................... C07D 487/04
See application file for complete search history.

(56) References Cited

U.S. PATENT DOCUMENTS

| | | |
|---|---|---|
| 8,765,774 B2 | 7/2014 | Gross et al. |
| 2004/0242596 A1 | 12/2004 | Kim et al. |

FOREIGN PATENT DOCUMENTS

| | | |
|---|---|---|
| WO | 2004009597 A2 | 1/2004 |
| WO | 2004099211 A1 | 11/2004 |
| WO | 2008107418 A1 | 9/2008 |
| WO | 2009068617 A1 | 6/2009 |
| WO | 2010100189 A1 | 9/2010 |
| WO | 2012102387 A1 | 8/2012 |

OTHER PUBLICATIONS

International Search Report from corresponding PCT/EP2014/060596, mailed Jul. 16, 2014.
Wang et al., "Rapid hit to lead evaluation of pyrazolo[3,4-d]pyrimidin-4-one as selective and orally bioavailable mGluR1 antagonists", Elsevier, ScienceDirect, Bioorganic & Medicinal Chemistry Letters 17, 2007, pp. 4303-4307.

*Primary Examiner* — Brian McDowell
(74) *Attorney, Agent, or Firm* — McBee Moore Woodward Vanik IP LLC

(57) ABSTRACT

The present application relates to the use of known and novel heterocyclic compounds for controlling animal pests, to novel heterocyclic compounds, to processes for preparation thereof and to the use thereof for controlling animal pests. The compounds are of formula (Ib)

14 Claims, No Drawings

HETEROCYCLIC COMPOUNDS AS PEST CONTROL AGENTS

CROSS REFERENCE TO RELATED APPLICATIONS

This application is a §371 National Stage Application of PCT/EP2014/060596, filed 23 May 2014, which claims priority to EP 13169415.0, filed 28 May 2013.

BACKGROUND

Field of the Invention

The present application relates to the use of known and novel heterocyclic compounds for controlling animal pests, to novel heterocyclic compounds, to processes for preparation thereof and to the use thereof for controlling animal pests.

Description of Related Art

WO 2012/102387 A1 describes heterocyclic compounds which can be used particularly as insecticides and acaricides.

Heterocyclic compounds for pharmaceutical applications are disclosed in WO 2004/009597 A2, WO 2008/107418 A1, WO 2009/068617 A1 and US 2004/242596 A1.

WO 2004/099211 A1 describes 6-cyclylmethyl- and 6-alkylmethyl-substituted pyrazolopyrimidines for pharmaceutical applications.

Bioorganic & Medicinal Chemistry Letters (2007), 17(15), 4303-4307 reports synthesis and pharmacological properties of particular pyrazolo[3,4-d]pyrimidin-4-ones.

Modern crop protection compositions have to meet many demands, for example in relation to efficacy, persistence and spectrum of their action and possible use. Questions of toxicity and of combinability with other active ingredients or formulation auxiliaries play a role, as does the question of the cost and effort involved in the synthesis of an active ingredient. In addition, resistances can occur. For all these reasons alone, the search for novel crop protection agents cannot be considered complete, and there is a constant need for novel compounds having improved properties compared to the known compounds, at least in relation to individual aspects.

SUMMARY

It was an object of the present invention to provide compounds which widen the spectrum of the pesticides under various aspects.

This object, and further objects which are not stated explicitly but can be discerned or derived from the connections discussed herein, are achieved by the use of compounds of the formula (I)

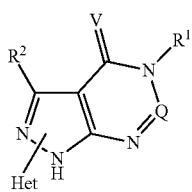

in which
Het is a radical from the group of

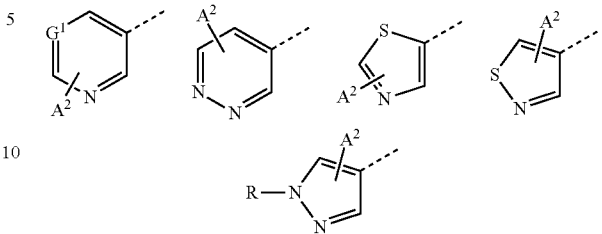

in which the dotted line represents the bond to one of the nitrogen atoms in the pyrazole ring and
$G^1$ is N or C-$A^1$,
$A^1$ is hydrogen, halogen, cyano, nitro, alkyl, haloalkyl, alkoxy, haloalkoxy or in each case optionally substituted cycloalkyl or cycloalkenyl,
$A^2$ is hydrogen, halogen, cyano, nitro, alkyl, haloalkyl, alkoxy, haloalkoxy or in each case optionally substituted cycloalkyl or cycloalkenyl,
R is hydrogen, alkyl, haloalkyl or optionally substituted cycloalkyl,
$R^1$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylsulphanylalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-substituted alkoxycarbonylalkyl, optionally halogen-substituted alkynyloxy, optionally halogen-substituted alkynyloxycarbonyl, dialkylaminocarbonyl, N-alkyl-N-cycloalkylaminocarbonyl, dialkylaminocarbonylalkyl, N-alkyl-N-cycloalkylaminocarbonylalkyl, heterocyclylcarbonylalkyl, alkylsulphanyl, haloalkylsulphanyl, alkylsulphinyl, haloalkylsulphinyl, alkylsulphonyl, haloalkylsulphonyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkyl, optionally halogen-, cyano-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkylcarbonyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkylalkyl, optionally substituted heterocyclyl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted heterocyclylalkyl, optionally halogen-, cyano-, nitro-, alkyl-, haloalkyl-, cycloalkyl- (which is optionally substituted), alkoxy- or haloalkoxy-substituted aryl, optionally halogen-, cyano-, alkyl-, haloalkyl-, cycloalkyl- (which is optionally substituted), alkoxy- or haloalkoxy-substituted arylalkyl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetaryl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl, $R^2$ is hydrogen or alkyl, Q is nitrogen or $C-R^3$ in which $R^3$ is a radical from the group of hydrogen, alkyl, haloalkyl, OH, alkoxy, haloalkoxy, SH, alkylsulphanyl, alkylsulphinyl, alkylsulphonyl, $NH_2$, alkylamino and dialkylamino, V is a radical from the group of oxygen, sulphur and $NR^4$ and $R^4$ is a radical from the group of hydrogen, cyano, alkyl, haloalkyl and cycloalkyl, for controlling animal pests.

Depending on the nitrogen atom to which the Het radical is bonded, the inventive compounds of the formula (I) can be represented by the formulae (Ia) and (Ib).

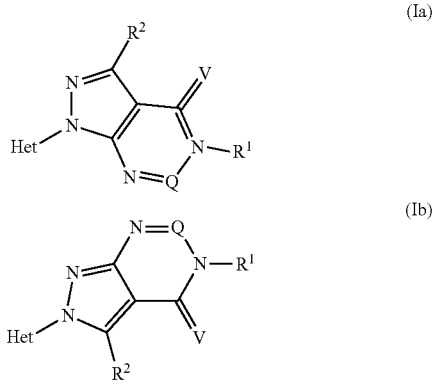

Unless mentioned otherwise, the compounds of the formulae (Ia) and (Ib) are always what is meant when compounds of the formula (I) are discussed.

DETAILED DESCRIPTION OF A PREFERRED EMBODIMENT

Preferred substituents or ranges for the radicals shown in the compounds of the formula (I) are elucidated below.

Het is a radical from the group of

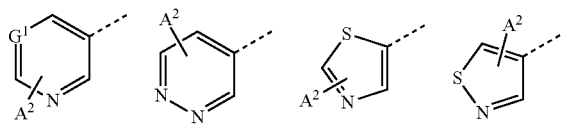

in which the dotted line represents the bond to one of the nitrogen atoms in the pyrazole ring.

$G^1$ is N or $C-A^1$.

$A^1$ is a radical from the group of hydrogen, halogen, $C_1-C_6$-alkyl and $C_1-C_4$-haloalkyl.

$A^2$ is a radical from the group of hydrogen, halogen, $C_1-C_6$-alkyl and $C_1-C_4$-haloalkyl.

R is a radical from the group of hydrogen, $C_1-C_6$-alkyl, $C_1-C_6$-haloalkyl and optionally mono- to tri-halogen-, -cyano-, -nitro-, —$C_1-C_3$-alkyl-, —$C_1-C_3$-alkoxy-substituted and mono-$C_3-C_6$-cycloalkyl-substituted $C_3-C_6$-cycloalkyl.

$R^1$ is a radical from the group of hydrogen, $C_1-C_6$-alkyl, $C_2-C_6$-haloalkyl, cyano-$C_1-C_6$-alkyl, $C_2-C_4$-alkenyl, $C_2-C_4$-haloalkenyl, $C_2-C_4$-alkynyl, $C_2-C_4$-haloalkynyl, $C_1-C_6$-alkoxy, $C_1-C_6$-haloalkoxy, optionally halogen-substituted $C_1-C_6$-alkoxy-$C_1-C_6$-alkyl, optionally halogen-substituted bis($C_1-C_6$-alkoxy)-$C_1-C_6$-alkyl, optionally halogen-substituted $C_1-C_6$-alkylsulphanyl-$C_1-C_6$-alkyl, optionally halogen-substituted $C_1-C_4$-alkylcarbonyl-$C_1-C_4$-alkyl, optionally halogen-substituted $C_1-C_6$-alkylsulphinyl-$C_1-C_6$-alkyl, optionally halogen-substituted $C_1-C_6$-alkylsulphonyl-$C_1-C_6$-alkyl, di($C_1-C_6$-alkyl)aminosulphanyl-$C_1-C_6$-alkyl, di($C_1-C_6$)alkylaminosulphinyl-$C_1-C_6$-alkyl, di($C_1-C_6$-alkyl)aminosulphonyl-$C_1-C_6$-alkyl, optionally halogen-substituted $C_1-C_6$-alkoxycarbonyl-$C_1-C_6$-alkyl, optionally halogen-substituted $C_2-C_4$-alkynyloxy, optionally halogen-substituted $C_2-C_4$-alkynyloxycarbonyl, di($C_1-C_6$-alkyl)aminocarbonyl, N—$C_1-C_6$-alkyl-N—$C_3-C_6$-cycloalkylaminocarbonyl, di($C_1-C_6$-alkyl)aminocarbonyl-($C_1-C_6$)alkyl, N—$C_1-C_6$-alkyl-N—$C_3-C_6$-cycloalkylaminocarbonyl-($C_1-C_6$)alkyl, heterocyclylcarbonyl-($C_1-C_6$)alkyl, $C_1-C_6$-alkylsulphanyl, $C_1-C_6$-haloalkylsulphanyl, $C_1-C_6$-alkylsulphinyl, $C_1-C_6$-haloalkylsulphinyl, $C_1-C_6$-alkylsulphonyl, $C_1-C_6$-haloalkylsulphonyl, optionally halogen-, cyano-, $C_1-C_6$-alkyl-, $C_1-C_6$-haloalkyl-, $C_1-C_6$-alkoxy-, $C_1-C_6$-haloalkoxy-, $C_1-C_6$-alkoxycarbonyl-, $C_1-C_6$-haloalkoxycarbonyl- or hetaryl-substituted (hetaryl itself optionally being substituted by $C_1-C_6$-alkyl or halogen) $C_3-C_6$-cycloalkyl, optionally halogen-, cyano-, $C_1-C_6$-alkyl-, $C_1-C_6$-haloalkyl-, $C_1-C_6$-alkoxy-, $C_1-C_6$-haloalkoxy-, $C_1-C_6$-alkoxycarbonyl-, $C_1-C_6$-haloalkoxycarbonyl- or hetaryl-substituted (hetaryl itself optionally being substituted by $C_1-C_6$-alkyl or halogen) $C_3-C_6$-cycloalkylcarbonyl, optionally halogen-, cyano-, $C_1-C_6$-alkyl-, $C_1-C_6$-haloalkyl-, $C_1-C_6$-alkoxy-, $C_1-C_6$-haloalkoxy-, $C_1-C_6$-alkoxycarbonyl-, $C_1-C_6$-haloalkoxycarbonyl- or hetaryl-substituted (hetaryl itself optionally being substituted by $C_1-C_6$-alkyl or halogen) $C_3-C_6$-cycloalkyl-$C_1-C_6$-alkyl, optionally halogen-, cyano- (including in the alkyl moiety), nitro-, $C_1-C_6$-alkyl-, $C_1-C_6$-haloalkyl-, $C_3-C_6$-cycloalkyl- (which is optionally substituted by halogen, cyano, $C_1-C_6$-alkyl and $C_3-C_6$-cycloalkyl), $C_1-C_6$-alkoxy-, $C_1-C_6$-haloalkoxy-, $C_1-C_6$-alkylthio-, $C_1-C_6$-haloalkylthio-, $C_1-C_6$-alkylsulphinyl-, $C_1-C_6$-alkylsulphonyl-, $C_1-C_6$-haloalkylsulphinyl-, $C_1-C_6$-haloalkylsulphonyl-, amino-, $C_1-C_6$-alkylamino-, di($C_1-C_6$-alkyl)amino-, $C_1-C_6$- alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted heterocyclyl-$C_1$-$C_6$-alkyl, optionally halogen-, cyano-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl, optionally halogen-, cyano-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl.

$R^2$ is hydrogen or $C_1$-$C_6$-alkyl.

Q is nitrogen or C—$R^3$.

$R^3$ is a radical from the group of hydrogen, $C_1$-$C_6$-alkyl, $C_1$-$C_6$-haloalkyl, OH, $C_1$-$C_6$-alkoxy, $C_1$-$C_6$-haloalkoxy, SH, $C_1$-$C_6$-alkylsulphanyl, $C_1$-$C_6$-alkylsulphinyl, $C_1$-$C_6$-alkylsulphonyl, $NH_2$, $C_1$-$C_6$-alkylamino and di($C_1$-$C_6$-alkyl)amino.

V is a radical from the group of oxygen, sulphur and $NR^4$.

$R^4$ is a radical from the group of hydrogen, cyano, $C_1$-$C_6$-alkyl, $C_2$-$C_6$-haloalkyl and $C_3$-$C_6$-cycloalkyl.

Particularly preferred substituents or ranges for the radicals shown in the compounds of the formula (I) are elucidated below.

Het is a radical from the group of

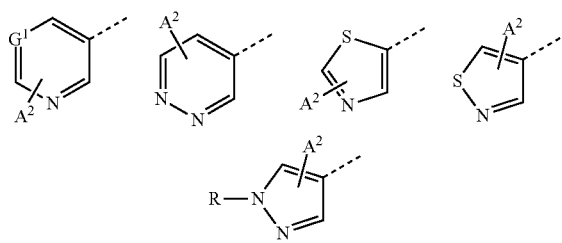

in which the dotted line represents the bond to one of the nitrogen atoms in the pyrazole ring.

$G^1$ is N or C-$A^1$.

$A^1$ is a radical from the group of hydrogen, halogen, $C_1$-$C_4$-alkyl and $C_1$-$C_4$-haloalkyl.

$A^2$ is a radical from the group of hydrogen, halogen, $C_1$-$C_4$-alkyl and $C_1$-$C_4$-haloalkyl.

R is hydrogen, $C_1$-$C_4$-alkyl, $C_1$-$C_4$-haloalkyl or optionally mono- to tri-halogen-, -cyano-, -nitro-, —$C_1$-$C_3$-alkyl-, —$C_1$-$C_3$-alkoxy-substituted and mono-$C_3$-$C_6$-cycloalkyl-substituted $C_3$-$C_6$-cycloalkyl.

$R^1$ is hydrogen, $C_1$-$C_6$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di($C_1$-$C_4$-alkyl)aminosulphanyl-$C_1$-$C_4$-alkyl, di($C_1$-$C_4$-alkyl)aminosulphinyl-$C_1$-$C_4$-alkyl, di($C_1$-$C_4$-alkyl)aminosulphonyl-$C_1$-$C_4$-alkyl, optionally halogen-substituted $C_1$-$C_4$-alkoxycarbonyl-$C_1$-$C_4$-alkyl, optionally halogen-substituted $C_2$-$C_4$-alkynyloxy, optionally halogen-substituted $C_2$-$C_4$-alkynyloxycarbonyl, di($C_1$-$C_4$-alkyl)aminocarbonyl, N—$C_1$-$C_4$-alkyl-N—$C_3$-$C_6$-cycloalkylaminocarbonyl, di($C_1$-$C_4$-alkyl)aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (pyridyl itself optionally being substituted by $C_1$-$C_4$-alkyl or halogen) $C_3$-$C_6$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (pyridyl itself optionally being substituted by $C_1$-$C_4$-alkyl or halogen) $C_3$-$C_6$-cycloalkylcarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl-, pyridyl-, pyrimidyl-, pyrazanyl-, pyridazinyl-, thiazolyl-, isothiazolyl-, thiadiazolyl-, oxazolyl-, isoxazolyl-, oxadiazolyl-, pyrazolyl-, triazinyl- or triazolyl-substituted (where these hetaryls are themselves optionally substituted by $C_1$-$C_4$-alkyl or halogen) $C_3$-$C_6$-cycloalkyl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted heterocyclyl-$C_1$-$C_4$-alkyl, optionally halogen-, cyano-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl, optionally halogen-, cyano-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl.

$R^2$ is hydrogen or $C_1$-$C_4$-alkyl.

Q is nitrogen or C—$R^3$.

$R^3$ is a radical from the group of hydrogen, $C_1$-$C_4$-alkyl, $C_1$-$C_4$-haloalkyl, OH, $C_1$-$C_4$-alkoxy, $C_1$-$C_4$-haloalkoxy, SH, $C_1$-$C_4$-alkylsulphanyl, $C_1$-$C_4$-alkylsulphinyl, $C_1$-$C_4$-alkylsulphonyl, $NH_2$, $C_1$-$C_4$-alkylamino and di($C_1$-$C_4$-alkyl)amino.

V is oxygen.

Very particularly preferred substituents or ranges of the radicals shown in the compounds of the formula (I) are elucidated below.

Het is a radical from the group of in which the dotted line represents the bond to one of the nitrogen atoms in the pyrazole ring.

$G^1$ is N or C-$A^1$.

$A^1$ is a radical from the group of hydrogen, fluorine, chlorine, bromine, methyl, ethyl, isopropyl, tert-butyl, trifluoromethyl, difluoromethyl, 2,2,2-trifluoroethyl, 2,2-difluoroethyl.

$A^2$ is a radical from the group of hydrogen, fluorine, chlorine, bromine, methyl, ethyl, isopropyl, tert-butyl, trifluoromethyl, difluoromethyl, 2,2,2-trifluoroethyl, 2,2-difluoroethyl.

R is a radical from the group of hydrogen, methyl, ethyl, isopropyl, tert-butyl, trifluoromethyl, difluoromethyl, 2,2,2-trifluoroethyl, 2,2-difluoroethyl, cyclopropyl or cyclobutyl.

$R^1$ is a radical from the group of hydrogen, methyl, ethyl, isopropyl, n-propyl, n-butyl, sec-butyl, tert-butyl, 2,2-dimethylpropyl, 2,2,2-trifluoroethyl, 2,2-difluoroethyl, 2,2-difluoro-n-propyl, methylsulphanylmethyl, methylsulphanylethyl, methylsulphanyl-n-propyl, 1-(methylsulphanyl)propan-2-yl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methyl-piperazin-1-ylcarbonylmethyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted heterocyclylmethyl and heterocyclylethyl, in each case cyclopropyl-substituted heterocyclylmethyl and heterocyclylethyl, wherein said cyclopropyl is optionally mono- or di-substituted by methyl, fluorine, chlorine, cyano or mono-substituted by cyclopropyl, optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted hetaryl, cyclopropyl-substituted hetaryl, wherein said cyclopropyl is optionally monoor di-substituted by methyl, fluorine, chlorine, cyano or mono-substituted by cyclopropyl, optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted aryl, cyclopropyl-substituted aryl, wherein said cyclopropyl is optionally mono- or di-substituted by methyl, fluorine, chlorine, cyano or mono-substituted by cyclopropyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted arylylmethyl and arylylethyl, in each case cyclopropyl-substituted arylmethyl and arylylethyl, wherein said cyclopropyl is optionally mono- or di-substituted by methyl, fluorine, chlorine, cyano or mono-substituted by cyclopropyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted hetarylmethyl and hetarylethyl, in each case cyclopropyl-substituted hetarylmethyl and hetarylethyl, wherein said cyclopropyl is optionally mono- or di-substituted by methyl, fluorine, chlorine, cyano or mono-substituted by cyclopropyl, $R^2$ is hydrogen or methyl.

Q is nitrogen or C—$R^3$.

$R^3$ is a radical from the group of hydrogen, methyl, ethyl, isopropyl, tert-butyl, cyclopropyl, cyclobutyl, trifluoromethyl, difluoromethyl and trifluoroethyl.

V is oxygen.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl is a saturated 4-, 5- or 6-membered ring containing 1 or 2 nitrogen atoms and/or one oxygen atom and/or one sulphur atom, for example azetidinyl, azolidinyl, azinanyl, oxetanyl, oxolanyl, oxanyl, dioxanyl, thiethanyl, thiolanyl, thianyl, piperazinyl, morpholinyl and tetrahydrofuryl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl and phenanthrenyl, and is preferably in turn phenyl, hetaryl (including as part of a larger unit, for example hetarylalkyl) is selected from the group of pyridyl, pyrimidyl, pyrazanyl, thiazolyl, isothiazolyl and pyridazinyl and heterocyclyl is selected from the group of azetidinyl, azolidinyl, azinanyl, oxetanyl, oxolanyl, oxanyl, dioxanyl, thiethanyl, thiolanyl, thianyl and tetrahydrofuryl.

In the very particularly preferred definitions, unless stated otherwise, aryl is phenyl, hetaryl (synonymous with heteroaryl, including as part of a larger unit, for example hetarylalkyl) is pyridyl, pyrimidyl, pyrazanyl and pyridazinyl and heterocyclyl is tetrahydrofuryl and dioxanyl.

Halogen-substituted radicals, for example haloalkyl, are mono- or polyhalogenated, up to the maximum number of possible substituents. In the case of polyhalogenation, the halogen atoms may be the same or different. Halogen here is fluorine, chlorine, bromine or iodine, especially fluorine, chlorine or bromine.

Saturated or unsaturated hydrocarbyl radicals, such as alkyl or alkenyl, may in each case be straight-chain or branched as far as possible, including in combination with heteroatoms, as, for example, in alkoxy.

Unless stated otherwise, optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference is given in accordance with the invention to using compounds of the formula (I) where a combination of the definitions listed above as preferred is present.

Particular preference is given in accordance with the invention to using compounds of the formula (I) where a combination of the definitions listed above as particularly preferred is present.

Very particular preference is given in accordance with the invention to using compounds of the formula (I) where a combination of the definitions listed above as very particularly preferred is present.

A preferred embodiment of the invention relates to compounds of the formula (Ia).

A further preferred embodiment of the invention relates to compounds of the formula (Ib).

A further preferred embodiment of the invention relates to compounds of the formula (Ia) in which Het is 3-pyridyl.

A further preferred embodiment of the invention relates to compounds of the formula (Ib) in which Het is 3-pyridyl.

A further preferred embodiment of the invention relates to compounds of the formula (Ib) in which Q is C—H.

The compounds of the formula (I) may also, where appropriate, depending on the nature of the substituents, be in the form of stereoisomers, i.e. in the form of geometric and/or optically active isomers or isomer mixtures of varying composition. This invention provides both the pure stereoisomers and any desired mixtures of these isomers, even if reference is generally made here only to compounds of the formula (I).

However, preference is given in accordance with the invention to using the optically active stereoisomeric forms of the compounds of the formula (I) and salts thereof.

The invention therefore relates both to the pure enantiomers and diastereomers and to mixtures thereof for controlling animal pests, including arthropods and particularly insects.

If Q is C—$R^3$ and $R^3$ is OH, SH or $NH_2$, the compounds of the formulae (Ia) and (Ib) may be present in tautomeric structures, as shown by way of example by the compounds of the formula (Ia) where $R^3$=OH:

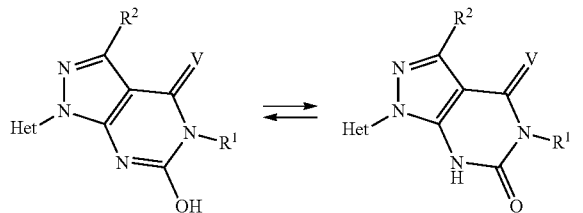

The tautomeric forms also form part of the subject-matter of the invention.

The application also relates to novel compounds of the formula (Ia)

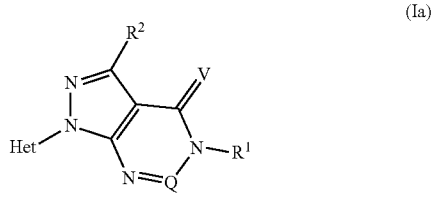

(Ia)

in which
Het is a radical from the group of

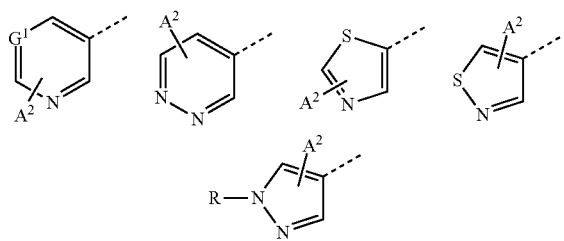

in which the dotted line represents the bond to one of the nitrogen atoms in the pyrazole ring and
$G^1$ is N or C-$A^1$,
$A^1$ is hydrogen, halogen, cyano, nitro, alkyl, haloalkyl, alkoxy, haloalkoxy or optionally substituted cycloalkyl or cycloalkenyl,
$A^2$ is hydrogen, halogen, cyano, nitro, alkyl, haloalkyl, alkoxy, haloalkoxy or optionally substituted cycloalkyl or cycloalkenyl,
R is hydrogen, alkyl, haloalkyl or optionally substituted cycloalkyl,
$R^1$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, in each case optionally halogen-substituted alkylsulphonylalkyl, dialkylaminosulphanylalkyl, dialkylaminosulphinylalkyl and dialkylaminosulphonylalkyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkylalkyl, optionally substituted heterocyclyl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted heterocyclylalkyl, optionally halogen-, cyano-, nitro-, alkyl-, haloalkyl-, cycloalkyl- (which is optionally substituted), alkoxy- or haloalkoxy-substituted aryl, optionally halogen-, cyano-, alkyl-, haloalkyl-, cycloalkyl- (which is optionally substituted), alkoxy- or haloalkoxy-substituted arylalkyl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetaryl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl,
$R^2$ is hydrogen or alkyl,
Q is nitrogen or C—$R^3$ in which
$R^3$ is a radical from the group of hydrogen, alkyl, haloalkyl, OH, alkoxy, haloalkoxy, SH, alkylsulphanyl, alkylsulphinyl, alkylsulphonyl, $NH_2$, alkylamino and dialkylamino,
V is a radical from the group of oxygen, sulphur and $NR^4$ and
$R^4$ is a radical from the group of hydrogen, cyano, alkyl, haloalkyl and cycloalkyl,
with the proviso that compounds in which $R^1$ is 4-chlorophenyl and, at the same time, Q is C, $R^3$ is methyl, V is O, $G^1$ is N or C-$A^1$ and $A^1$ and $A^2$ are each H are excluded, and that additionally excluded are compounds in which $R^1$ is 3-chlorophenyl or optionally substituted cycloalkyl and, at the same time, Q is C—$R^3$, $R^3$ is hydrogen and V is O.

Preferred substituents or ranges for the radicals shown in the compounds of the formula (Ia) are elucidated below.

Het is a radical from the group of

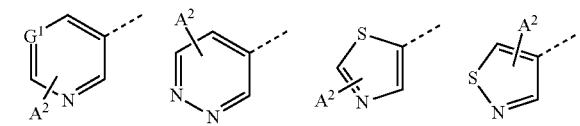

in which the dotted line represents the bond to one of the nitrogen atoms in the pyrazole ring.

$G^1$ is N or $C-A^1$.

$A^1$ is a radical from the group of hydrogen, halogen, $C_1$-$C_6$-alkyl and $C_1$-$C_4$-haloalkyl.

$A^2$ is a radical from the group of hydrogen, halogen, $C_1$-$C_6$-alkyl and $C_1$-$C_4$-haloalkyl.

R is a radical from the group of hydrogen, $C_1$-$C_6$-alkyl, $C_1$-$C_6$-haloalkyl and optionally mono- to tri-halogen-, -cyano-, -nitro-, —$C_1$-$C_3$-alkyl-, —$C_1$-$C_3$-alkoxy- and —$C_3$-$C_6$-cycloalkyl-substituted $C_3$-$C_6$-cycloalkyl.

$R^1$ is a radical from the group of hydrogen, $C_1$-$C_6$-alkyl, $C_2$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylsulphanyl-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, di($C_1$-$C_6$-alkyl)aminosulphanyl-$C_1$-$C_6$-alkyl, di($C_1$-$C_6$-alkyl)aminosulphinyl-$C_1$-$C_6$-alkyl, di($C_1$-$C_6$-alkyl)aminosulphonyl-$C_1$-$C_6$-alkyl, optionally halogen-substituted $C_1$-$C_6$-alkoxycarbonyl-$C_1$-$C_6$-alkyl, optionally halogen-substituted $C_2$-$C_4$-alkynyloxy, optionally halogen-substituted $C_2$-$C_4$-alkynyloxycarbonyl, di($C_1$-$C_6$-alkyl)aminocarbonyl, N—$C_1$-$C_6$-alkyl-N—$C_3$-$C_6$-cycloalkylaminocarbonyl, di($C_1$-$C_6$-alkyl)aminocarbonyl-($C_1$-$C_6$)alkyl, N—$C_1$-$C_6$-alkyl-N—$C_3$-$C_6$-cycloalkylaminocarbonyl-($C_1$-$C_6$)alkyl, heterocyclylcarbonyl-($C_1$-$C_6$)alkyl, $C_1$-$C_6$-alkylsulphanyl, $C_1$-$C_6$-haloalkylsulphanyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (hetaryl itself optionally being substituted by $C_1$-$C_6$-alkyl or halogen) $C_3$-$C_6$-cycloalkyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (hetaryl itself optionally being substituted by $C_1$-$C_6$-alkyl or halogen) $C_3$-$C_6$-cycloalkylcarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (hetaryl itself optionally being substituted by $C_1$-$C_6$-alkyl or halogen) $C_3$-$C_6$-cycloalkyl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted heterocyclyl-$C_1$-$C_6$-alkyl, optionally halogen-, cyano-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl, optionally halogen-, cyano-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl.

$R^2$ is hydrogen or $C_1$-$C_6$-alkyl.

Q is nitrogen or C—$R^3$.

$R^3$ is a radical from the group of hydrogen, $C_1$-$C_6$-alkyl, $C_1$-$C_6$-haloalkyl, OH, $C_1$-$C_6$-alkoxy, $C_1$-$C_6$-haloalkoxy, SH, $C_1$-$C_6$-alkylsulphanyl, $C_1$-$C_6$-alkylsulphinyl, $C_1$-$C_6$-alkylsulphonyl, $NH_2$, $C_1$-$C_6$-alkylamino and di($C_1$-$C_6$-alkyl)amino.

V is a radical from the group of oxygen, sulphur and $NR^4$.

$R^4$ is a radical from the group of hydrogen, cyano, $C_1$-$C_6$-alkyl, $C_2$-$C_6$-haloalkyl and $C_3$-$C_6$-cycloalkyl.

Particularly preferred substituents or ranges for the radicals shown in the compounds of the formula (Ia) are elucidated below.

Het is a radical from the group of

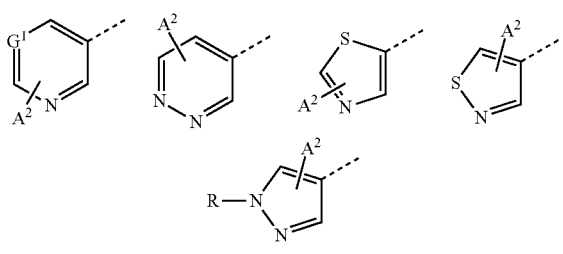

in which the dotted line represents the bond to one of the nitrogen atoms in the pyrazole ring.

$G^1$ is N or $C-A^1$.

$A^1$ is a radical from the group of hydrogen, halogen, $C_1$-$C_4$-alkyl and $C_1$-$C_4$-haloalkyl.

$A^2$ is a radical from the group of hydrogen, halogen, $C_1$-$C_4$-alkyl and $C_1$-$C_4$-haloalkyl.

R is hydrogen, $C_1$-$C_4$-alkyl, $C_1$-$C_4$-haloalkyl or optionally mono- to tri-halogen-, -cyano-, -nitro-, —$C_1$-$C_3$-alkyl-, —$C_1$-$C_3$-alkoxy- and —$C_3$-$C_6$-cycloalkyl-substituted $C_3$-$C_6$-cycloalkyl.

$R^1$ is hydrogen, $C_1$-$C_6$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di($C_1$-$C_4$-alkyl)aminosulphanyl-$C_1$-$C_4$-alkyl, di($C_1$-$C_4$-alkyl)aminosulphinyl-$C_1$-$C_4$-alkyl, di($C_1$-$C_4$-alkyl)aminosulphonyl-$C_1$-$C_4$-alkyl, optionally halogen-substituted $C_1$-$C_4$-alkoxycarbonyl-$C_1$-$C_4$-alkyl, optionally halogen-substituted $C_2$-$C_4$-alkynyloxy, optionally halogen-substituted $C_2$-$C_4$-alkynyloxycarbonyl, di($C_1$-$C_4$-alkyl)aminocarbonyl, N—$C_1$-$C_4$-alkyl-N—$C_3$-$C_6$-cycloalkylaminocarbonyl, di($C_1$-$C_4$-alkyl)aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (pyridyl itself optionally being substituted by $C_1$-$C_4$-alkyl or halogen) $C_3$-$C_6$-cycloalkyl, optionally halogen-, cyano-, $C_1$-$C_4$-alkyl, —$C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (pyridyl itself optionally being substituted by $C_1$-$C_4$-alkyl or halogen) $C_3$-$C_6$-cycloalkylcarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl-, pyridyl-, pyrimidyl-, pyrazanyl-, pyridazinyl-, thiazolyl-, isothiazolyl-, thiadiazolyl-, oxazolyl-, isoxazolyl-, oxadiazolyl-, pyrazolyl-, triazinyl- or triazolyl-substituted (which is itself optionally substituted by $C_1$-$C_4$-alkyl or halogen) $C_3$-$C_6$-cycloalkyl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted heterocyclyl-$C_1$-$C_4$-alkyl, optionally halogen-, cyano-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl, optionally halogen-, cyano-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl.

$R^2$ is hydrogen or $C_1$-$C_4$-alkyl.

Q is nitrogen or C—$R^3$.

$R^3$ is a radical from the group of hydrogen, $C_1$-$C_4$-alkyl, $C_1$-$C_4$-haloalkyl, OH, $C_1$-$C_4$-alkoxy, $C_1$-$C_4$-haloalkoxy, SH, $C_1$-$C_4$-alkylsulphanyl, $C_1$-$C_4$-alkylsulphinyl, $C_1$-$C_4$-alkylsulphonyl, $NH_2$, $C_1$-$C_4$-alkylamino and di($C_1$-$C_4$-alkyl)amino.

V is oxygen.

Very particularly preferred substituents or ranges of the radicals shown in the compounds of the formula (Ia) are elucidated below.

Het is a radical from the group of

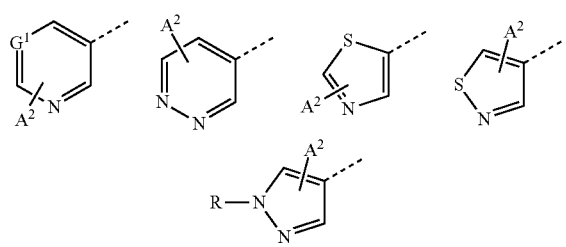

in which the dotted line represents the bond to one of the nitrogen atoms in the pyrazole ring.

$G^1$ is N or $C-A^1$.

$A^1$ is a radical from the group of hydrogen, fluorine, chlorine, bromine, methyl, ethyl, isopropyl, tert-butyl, trifluoromethyl, difluoromethyl, 2,2,2-trifluoroethyl, 2,2-difluoroethyl.

$A^2$ is a radical from the group of hydrogen, fluorine, chlorine, bromine, methyl, ethyl, isopropyl, tert-butyl, trifluoromethyl, difluoromethyl, 2,2,2-trifluoroethyl, 2,2-difluoroethyl.

R is a radical from the group of hydrogen, methyl, ethyl, isopropyl, tert-butyl, trifluoromethyl, difluoromethyl, 2,2,2-trifluoroethyl, 2,2-difluoroethyl, cyclopropyl or cyclobutyl.

$R^1$ is a radical from the group of hydrogen, methyl, ethyl, isopropyl, n-propyl, n-butyl, sec-butyl, tert-butyl, 2,2-dimethylpropyl, 2,2,2-trifluoroethyl, 2,2-difluoroethyl, 2,2-difluoro-n-propyl, methylsulphanylmethyl, methylsulphanylethyl, methylsulphanyl-n-propyl, 1-(methylsulphanyl)propan-2-yl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted heterocyclylmethyl and heterocyclylethyl, in each case cyclopropyl-substituted heterocyclylmethyl and heterocyclylethyl, wherein said cyclopropyl is optionally mono- or di-substituted by methyl, fluorine, chlorine, cyano or mono-substituted by cyclopropyl, optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted hetaryl, cyclopropyl-substituted hetaryl, wherein said cyclopropyl is optionally mono- or di-substituted by methyl, fluorine, chlorine, cyano or mono-substituted by cyclopropyl, optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted aryl, cyclopropyl-substituted aryl, wherein said cyclopropyl is optionally mono- or di-substituted by methyl, fluorine, chlorine, cyano or mono-substituted by cyclopropyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted arylmethyl and arylethyl, in each case cyclopropyl-substituted arylmethyl and arylethyl, wherein said cyclopropyl is optionally mono- or di-substituted by methyl, fluorine, chlorine, cyano or mono-substituted by cyclopropyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted hetarylmethyl and hetarylethyl, in each case cyclopropyl-substituted hetarylmethyl and hetarylethyl, wherein said cyclopropyl is optionally mono- or di-substituted by methyl, fluorine, chlorine, cyano or mono-substituted by cyclopropyl, $R^2$ is hydrogen or methyl.

Q is nitrogen or $C-R^3$.

$R^3$ is a radical from the group of hydrogen, methyl, ethyl, isopropyl, tert-butyl, cyclopropyl, cyclobutyl, trifluoromethyl, difluoromethyl and trifluoroethyl.

V is oxygen.

For the novel compounds of the formula (Ia), the following applies in each case: compounds in which $R^1$ is 4-chlorophenyl and, at the same time, Q is C, $R^3$ is methyl, V is O, $G^1$ is N or C-$A^1$ and $A^1$ and $A^2$ are each H are excluded, and additionally excluded are compounds in which $R^1$ is 3-chlorophenyl or optionally substituted cycloalkyl and, at the same time, Q is $C-R^3$, $R^3$ is hydrogen and V is O.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl is a saturated 4-, 5- or 6-membered ring containing 1 or 2 nitrogen atoms and/or one oxygen atom and/or one sulphur atom, for example azetidinyl, azolidinyl, azinanyl, oxetanyl, oxolanyl, oxanyl, dioxanyl, thiethanyl, thiolanyl, thianyl, piperazinyl, morpholinyl and tetrahydrofuryl.

In the particularly preferred definitions, unless stated otherwise,
halogen is selected from the group of fluorine, chlorine, bromine and iodine, preferably in turn from the group of fluorine, chlorine and bromine,
aryl (including as part of a larger unit, for example arylalkyl) is selected from the group of phenyl, naphthyl, anthryl, phenanthrenyl, and is preferably in turn phenyl,
hetaryl (including as part of a larger unit, for example hetarylalkyl) is selected from the group of pyridyl, pyrimidyl, pyrazanyl, thiazolyl, isothiazolyl and pyridazinyl.
Heterocyclyl is azetidinyl, azolidinyl, azinanyl, oxetanyl, oxolanyl, oxanyl, dioxanyl, thiethanyl, thiolanyl, thianyl and tetrahydrofuryl.

In the very particularly preferred definitions, unless stated otherwise,
aryl is phenyl,
hetaryl (synonymous with heteroaryl, including as part of a larger unit, for example hetarylalkyl) is pyridyl, pyrimidyl, pyrazanyl and pyridazinyl and
heterocyclyl is tetrahydrofuryl and dioxanyl.

Halogen-substituted radicals, for example haloalkyl, are mono- or polyhalogenated, up to the maximum number of possible substituents. In the case of polyhalogenation, the halogen atoms may be the same or different. In this case, halogen is fluorine, chlorine, bromine or iodine, especially fluorine, chlorine or bromine.

Saturated or unsaturated hydrocarbyl radicals, such as alkyl or alkenyl, may in each case be straight-chain or branched as far as possible, including in combination with heteroatoms, as, for example, in alkoxy.

Unless stated otherwise, optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference is given in accordance with the invention to novel compounds of the formula (Ia) in which a combination of the definitions listed above as preferred is present.

Particular preference is given in accordance with the invention to novel compounds of the formula (Ia) in which a combination of the definitions listed above as particularly preferred is present.

Very particular preference is given in accordance with the invention to novel compounds of the formula (Ia) in which a combination of the definitions listed above as very particularly preferred is present.

Explicitly very particular preference is given in accordance with the invention to novel compounds of the formula (Ia) in which a combination of the definitions listed above as explicitly very particularly preferred is present.

The application also relates to novel compounds of the formula (Ib)

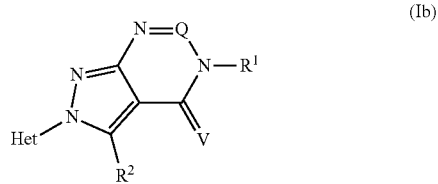

in which
Het is a radical from the group of

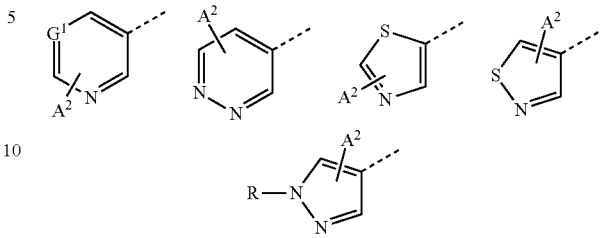

in which the dotted line represents the bond to one of the nitrogen atoms in the pyrazole ring and
$G^1$ is N or C-$A^1$,
$A^1$ is hydrogen, halogen, cyano, nitro, alkyl, haloalkyl, alkoxy, haloalkoxy or in each case optionally substituted cycloalkyl or cycloalkenyl,
$A^2$ is hydrogen, halogen, cyano, nitro, alkyl, haloalkyl, alkoxy, haloalkoxy or in each case optionally substituted cycloalkyl or cycloalkenyl,
R is hydrogen, alkyl, haloalkyl or optionally substituted cycloalkyl,
$R^1$ is a radical from the group of hydrogen, alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkylalkyl, optionally substituted heterocyclyl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted heterocyclylalkyl, optionally halogen-, cyano-, nitro-, alkyl-, haloalkyl-, cycloalkyl- (which is optionally substituted), alkoxy- or haloalkoxy-substituted aryl, optionally halogen-, cyano-, alkyl-, haloalkyl-, cycloalkyl- (which is optionally substituted), alkoxy- or haloalkoxy-substituted arylalkyl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetaryl, optionally halogen-, cyano- (including in the alkyl moiety), nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl, $R^2$ is hydrogen or alkyl, Q is nitrogen or C—$R^3$ in which $R^3$ is a radical from the group of hydrogen, alkyl, haloalkyl, OH, alkoxy, haloalkoxy, SH, alkylsulphanyl, alkylsulphinyl, alkylsulphonyl, $NH_2$, alkylamino and dialkylamino, V is a radical from the group of oxygen, sulphur and $NR^4$ and $R^4$ is a radical from the group of hydrogen, cyano, alkyl, haloalkyl and cycloalkyl, with the proviso that compounds in which $R^1$ is phenyl or 4-chlorophenyl and, at the same time, Q is C, $R^3$ is methyl, V is O, $G^1$ is N or C-$A^1$ and $A^1$ and $A^2$ are each H are excluded.

Preferred substituents or ranges for the radicals shown in the compounds of the formula (Ib) are elucidated below.

Het is a radical from the group of

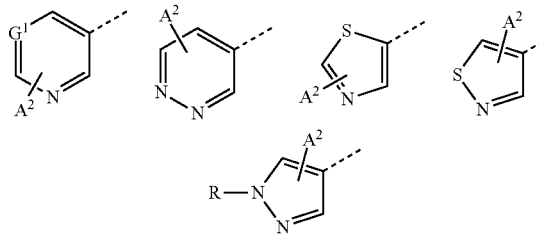

in which the dotted line represents the bond to one of the nitrogen atoms in the pyrazole ring.

$G^1$ is N or C-$A^1$.

$A^1$ is a radical from the group of hydrogen, halogen, $C_1$-$C_6$-alkyl and $C_1$-$C_4$-haloalkyl.

$A^2$ is a radical from the group of hydrogen, halogen, $C_1$-$C_6$-alkyl and $C_1$-$C_4$-haloalkyl.

R is a radical from the group of hydrogen, $C_1$-$C_6$-alkyl, $C_1$-$C_6$-haloalkyl and optionally mono- to tri-halogen-, -cyano-, -nitro-, —$C_1$-$C_3$-alkyl-, —$C_1$-$C_3$-alkoxy- and —$C_3$-$C_6$-cycloalkyl-substituted $C_3$-$C_6$-cycloalkyl.

$R^1$ is a radical from the group of hydrogen, $C_1$-$C_6$-alkyl, $C_2$-$C_6$-haloalkyl, cyano-$C_1$-$C_6$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_6$-alkoxy, $C_1$-$C_6$-haloalkoxy, optionally halogen-substituted $C_1$-$C_6$-alkoxy-$C_1$-$C_6$-alkyl, optionally halogen-substituted bis($C_1$-$C_6$-alkoxy)-$C_1$-$C_6$-alkyl, optionally halogen-substituted $C_1$-$C_6$-alkylsulphanyl-$C_1$-$C_6$-alkyl, optionally halogen-substituted $C_1$-$C_4$-alkylcarbonyl-$C_1$-$C_4$-alkyl, optionally halogen-substituted $C_1$-$C_6$-alkylsulphinyl-$C_1$-$C_6$-alkyl, optionally halogen-substituted $C_1$-$C_6$-alkylsulphonyl-$C_1$-$C_6$-alkyl, di($C_1$-$C_6$-alkyl)aminosulphanyl-$C_1$-$C_6$-alkyl, di($C_1$-$C_6$-alkyl)aminosulphinyl-$C_1$-$C_6$-alkyl, di($C_1$-$C_6$-alkyl)aminosulphonyl-$C_1$-$C_6$-alkyl, optionally halogen-substituted $C_1$-$C_6$-alkoxycarbonyl-$C_1$-$C_6$-alkyl, optionally halogen-substituted $C_2$-$C_4$-alkynyloxy, optionally halogen-substituted $C_2$-$C_4$-alkynyloxycarbonyl, di($C_1$-$C_6$-alkyl) aminocarbonyl, N—$C_1$-$C_6$-alkyl-N—$C_3$-$C_6$-cycloalkylaminocarbonyl, di($C_1$-$C_6$-alkyl) aminocarbonyl-($C_1$-$C_6$)alkyl, N—$C_1$-$C_6$-alkyl-N—$C_3$-$C_6$-cycloalkylaminocarbonyl-($C_1$-$C_6$)alkyl, heterocyclylcarbonyl-($C_1$-$C_6$)alkyl, $C_1$-$C_6$-alkylsulphanyl, $C_1$-$C_6$-haloalkylsulphanyl, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (hetaryl itself optionally being substituted by $C_1$-$C_6$-alkyl or halogen) $C_3$-$C_6$-cycloalkyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (hetaryl itself optionally being substituted by $C_1$-$C_6$-alkyl or halogen) $C_3$-$C_6$-cycloalkylcarbonyl, optionally halogen-, cyano-, $C_1$-$C_6$-alkyl-, $C_1$-$C_6$-haloalkyl-, $C_1$-$C_6$-alkoxy-, $C_1$-$C_6$-haloalkoxy-, $C_1$-$C_6$-alkoxycarbonyl-, $C_1$-$C_6$-haloalkoxycarbonyl- or hetaryl-substituted (hetaryl itself optionally being substituted by $C_1$-$C_6$-alkyl or halogen) $C_3$-$C_6$-cycloalkyl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted heterocyclyl-$C_1$-$C_6$-alkyl, optionally halogen-, cyano-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl, optionally halogen-, cyano-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy- or $C_1$-$C_6$-haloalkoxy-substituted aryl-$C_1$-$C_6$-alkyl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl, optionally halogen-, cyano- (including in the alkyl moiety), nitro-, $C_1$-$C_6$-alkyl-, $C_1$-$C_6$-haloalkyl-, $C_3$-$C_6$-cycloalkyl- (which is optionally substituted by halogen, cyano, $C_1$-$C_6$-alkyl and $C_3$-$C_6$-cycloalkyl), $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-alkylsulphonyl-, $C_1$-$C_6$-haloalkylsulphinyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$- alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted hetaryl-$C_1$-$C_6$-alkyl.

$R^2$ is hydrogen or $C_1$-$C_6$-alkyl.

Q is nitrogen or C—$R^3$.

$R^3$ is a radical from the group of hydrogen, $C_1$-$C_6$-alkyl, $C_1$-$C_6$-haloalkyl, OH, $C_1$-$C_6$-alkoxy, $C_1$-$C_6$-haloalkoxy, SH, $C_1$-$C_6$-alkylsulphanyl, $C_1$-$C_6$-alkylsulphinyl, $C_1$-$C_6$-alkylsulphonyl, $NH_2$, $C_1$-$C_6$-alkylamino and di($C_1$-$C_6$-alkyl)amino.

V is a radical from the group of oxygen, sulphur and $NR^4$.

$R^4$ is a radical from the group of hydrogen, cyano, $C_1$-$C_6$-alkyl, $C_2$-$C_6$-haloalkyl and $C_3$-$C_6$-cycloalkyl.

Particularly preferred substituents or ranges for the radicals shown in the compounds of the formula (Ib) are elucidated below.

Het is a radical from the group of

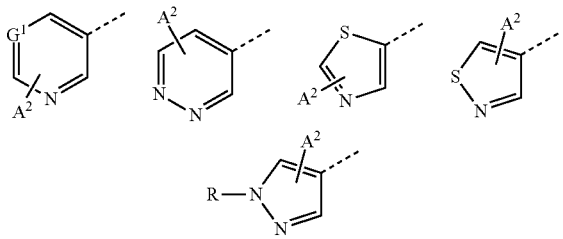

in which the dotted line represents the bond to one of the nitrogen atoms in the pyrazole ring.

$G^1$ is N or C-$A^1$.

$A^1$ is a radical from the group of hydrogen, halogen, $C_1$-$C_4$-alkyl and $C_1$-$C_4$-haloalkyl.

$A^2$ is a radical from the group of hydrogen, halogen, $C_1$-$C_4$-alkyl and $C_1$-$C_4$-haloalkyl.

R is a radical from the group of hydrogen, $C_1$-$C_4$-alkyl, $C_1$-$C_4$-haloalkyl and optionally mono- to tri-halogen-, -cyano-, -nitro-, —$C_1$-$C_3$-alkyl-, —$C_1$-$C_3$-alkoxy- and —$C_3$-$C_6$-cycloalkyl-substituted $C_3$-$C_6$-cycloalkyl.

$R^1$ is a radical from the group of hydrogen, $C_1$-$C_6$-alkyl, $C_2$-$C_4$-haloalkyl, cyano-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_1$-$C_4$-alkoxy, $C_1$-$C_4$-haloalkoxy, optionally halogen-substituted $C_1$-$C_2$-alkoxy-$C_1$-$C_4$-alkyl, optionally halogen-substituted bis($C_1$-$C_2$-alkoxy)-$C_1$-$C_4$-alkyl, optionally halogen-substituted $C_1$-$C_4$-alkylsulphanyl-$C_1$-$C_4$-alkyl, optionally halogen-substituted $C_1$-$C_4$-alkylcarbonyl-$C_1$-$C_4$-alkyl, optionally halogen-substituted $C_1$-$C_4$-alkylsulphinyl-$C_1$-$C_4$-alkyl, optionally halogen-substituted $C_1$-$C_4$-alkylsulphonyl-$C_1$-$C_4$-alkyl, di($C_1$-$C_4$-alkyl)aminosulphanyl-$C_1$-$C_4$-alkyl, di($C_1$-$C_4$-alkyl)aminosulphinyl-$C_1$-$C_4$-alkyl, di($C_1$-$C_4$-alkyl)aminosulphonyl-$C_1$-$C_4$-alkyl, optionally halogen-substituted $C_1$-$C_4$-alkoxycarbonyl-$C_1$-$C_4$-alkyl, optionally halogen-substituted $C_2$-$C_4$-alkynyloxy, optionally halogen-substituted $C_2$-$C_4$-alkynyloxycarbonyl, di($C_1$-$C_4$-alkyl)aminocarbonyl, N—$C_1$-$C_4$-alkyl-N—$C_3$-$C_6$-cycloalkylaminocarbonyl, di($C_1$-$C_4$-alkyl)aminocarbonyl-$C_1$-$C_4$-alkyl, N—$C_1$-$C_4$-alkyl-N—$C_3$-$C_6$-cycloalkylaminocarbonyl-$C_1$-$C_4$-alkyl, heterocyclylcarbonyl-$C_1$-$C_4$-alkyl, $C_1$-$C_4$-alkylsulphanyl, $C_1$-$C_4$-haloalkylsulphanyl, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (pyridyl itself optionally being substituted by $C_1$-$C_4$-alkyl or halogen) $C_3$-$C_6$-cycloalkyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl- or pyridyl-substituted (pyridyl itself optionally being substituted by $C_1$-$C_4$-alkyl or halogen) $C_3$-$C_6$-cycloalkylcarbonyl, optionally halogen-, cyano-, $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkoxycarbonyl-, $C_1$-$C_4$-haloalkoxycarbonyl-, pyridyl-, pyrimidyl-, pyrazanyl-, pyridazinyl-, thiazolyl-, isothiazolyl-, thiadiazolyl-, oxazolyl-, isoxazolyl-, oxadiazolyl-, pyrazolyl-, triazinyl- or triazolyl-substituted (which is itself optionally substituted by $C_1$-$C_4$-alkyl or halogen) $C_3$-$C_6$-cycloalkyl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted heterocyclyl-$C_1$-$C_4$-alkyl, optionally halogen-, cyano-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl, optionally halogen-, cyano-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy- or $C_1$-$C_4$-haloalkoxy-substituted aryl-$C_1$-$C_4$-alkyl, optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl optionally halogen-, cyano- (including in the alkyl moiety), nitro-, $C_1$-$C_4$-alkyl-, $C_1$-$C_4$-haloalkyl-, $C_3$-$C_6$-cycloalkyl- (which is optionally substituted by halogen, cyano, $C_1$-$C_4$-alkyl and $C_3$-$C_6$-cycloalkyl), $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-alkylsulphonyl-, $C_1$-$C_4$-haloalkylsulphinyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted hetaryl-$C_1$-$C_4$-alkyl.

R² is hydrogen or $C_1$-$C_4$-alkyl.

Q is nitrogen or C—R³.

R³ is a radical from the group of hydrogen, $C_1$-$C_4$-alkyl, $C_1$-$C_4$-haloalkyl, OH, $C_1$-$C_4$-alkoxy, $C_1$-$C_4$-haloalkoxy, SH, $C_1$-$C_4$-alkylsulphanyl, $C_1$-$C_4$-alkylsulphinyl, $C_1$-$C_4$-alkylsulphonyl, $NH_2$, $C_1$-$C_4$-alkylamino and di($C_1$-$C_4$-alkyl)amino.

V is oxygen.

Very particularly preferred substituents or ranges of the radicals shown in the compounds of the formula (Ib) are elucidated below.

Het is a radical from the group of

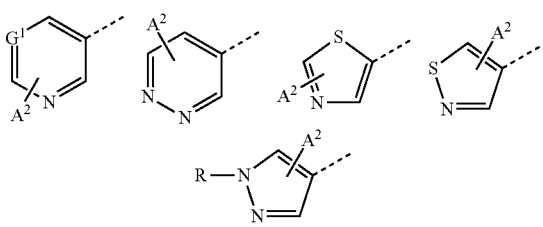

in which the dotted line represents the bond to one of the nitrogen atoms in the pyrazole ring.

G¹ is N or C-A¹.

A¹ is a radical from the group of hydrogen, fluorine, chlorine, bromine, methyl, ethyl, isopropyl, tert-butyl, trifluoromethyl, difluoromethyl, 2,2,2-trifluoroethyl, 2,2-difluoroethyl.

A² is a radical from the group of hydrogen, fluorine, chlorine, bromine, methyl, ethyl, isopropyl, tert-butyl, trifluoromethyl, difluoromethyl, 2,2,2-trifluoroethyl, 2,2-difluoroethyl.

R is a radical from the group of hydrogen, methyl, ethyl, isopropyl, tert-butyl, trifluoromethyl, difluoromethyl, 2,2,2-trifluoroethyl, 2,2-difluoroethyl, cyclopropyl or cyclobutyl.

R¹ is a radical from the group of hydrogen, methyl, ethyl, isopropyl, n-propyl, n-butyl, sec-butyl, tert-butyl, 2,2-dimethylpropyl, 2,2,2-trifluoroethyl, 2,2-difluoroethyl, 2,2-difluoro-n-propyl, methylsulphanylmethyl, methylsulphanylethyl, methylsulphanyl-n-propyl, 1-(methylsulphanyl)propan-2-yl, trifluoromethylsulphonylmethyl, ethylsulphonylmethyl, 2,2,2-trifluoroethylsulphonylmethyl, 2,2-difluoroethylsulphonylmethyl, isopropylsulphanylmethyl, methylsulphinylmethyl, trifluoromethylsulphinylmethyl, ethylsulphinylmethyl, 2,2,2-trifluoroethylsulphinylmethyl, 2,2-difluoroethylsulphinylmethyl, isopropylsulphinylmethyl, methylsulphonylmethyl, trifluoromethylsulphonylmethyl, ethylsulphonylmethyl, 2,2,2-trifluoroethylsulphonylmethyl, 2,2-difluoroethylsulphonylmethyl, isopropylsulphonylmethyl, methoxycarbonylmethyl, ethoxycarbonylmethyl, methoxycarbonylethyl, ethoxycarbonylethyl, dimethylaminocarbonyl, diethylaminocarbonyl, N-ethyl-N-methylaminocarbonyl, N-isopropyl-N-methylaminocarbonyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, methylsulphanyl, trifluoromethylsulphanyl, ethylsulphanyl, 2,2,2-trifluoroethylsulphanyl, 2,2-difluoroethylsulphanyl, isopropylsulphanyl, methylsulphinyl, trifluoromethylsulphinyl, ethylsulphinyl, 2,2,2-trifluoroethylsulphinyl, 2,2-difluoroethylsulphinyl, isopropylsulphinyl, methylsulphonyl, trifluoromethylsulphonyl, ethylsulphonyl, 2,2,2-trifluoroethylsulphonyl, 2,2-difluoroethylsulphonyl, isopropylsulphonyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, cyclobutyl, cyclopentyl, cyclohexyl, 4-trifluoromethylcyclohexyl, cyclopropylmethyl, cyclopropylethyl, cyclobutylmethyl, N-cyclopropyl-N-methylaminocarbonyl, morpholin-4-ylcarbonylmethyl, piperazin-1-ylcarbonylmethyl, 4-methylpiperazin-1-ylcarbonylmethyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted heterocyclylmethyl and heterocyclylethyl, in each case cyclopropyl-substituted heterocyclylmethyl and heterocyclylethyl, wherein said cyclopropyl is optionally mono- or di-substituted by methyl, fluorine, chlorine, cyano or mono-substituted by cyclopropyl, optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted hetaryl, cyclopropyl-substituted hetaryl, wherein said cyclopropyl is optionally mono- or di-substituted by methyl, fluorine, chlorine, cyano or mono-substituted by cyclopropyl, optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted aryl, cyclopropyl-substituted aryl, wherein said cyclopropyl is optionally mono- or di-substituted by methyl, fluorine, chlorine, cyano or mono-substituted by cyclopropyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted arylylmethyl and arylylethyl, in each case cyclopropyl-substituted arylmethyl and arylylethyl, wherein said cyclopropyl is optionally mono- or di-substituted by methyl, fluorine, chlorine, cyano or mono-substituted by cyclopropyl, in each case optionally singly to triply, identically or differently halogen-, cyano-, nitro-, methyl-, ethyl-, isopropyl-, tert-butyl-, trifluoromethyl-, difluoromethyl-, methoxy-, trifluoromethoxy- or difluoromethoxy-substituted hetarylmethyl and hetarylethyl, in each case cyclopropyl-substituted hetarylmethyl and hetarylethyl, wherein said cyclopropyl is optionally mono- or di-substituted by methyl, fluorine, chlorine, cyano or mono-substituted by cyclopropyl.

R² is hydrogen or methyl.

Q is nitrogen or C—R³.

R³ is a radical from the group of hydrogen, methyl, ethyl, isopropyl, tert-butyl, cyclopropyl, cyclobutyl, trifluoromethyl, difluoromethyl and trifluoroethyl.

V is oxygen.

For the novel compounds of the formula (Ib), the following applies in each case: compounds in which R¹ is phenyl or 4-chlorophenyl and, at the same time, Q is C, R³ is methyl, V is O, G¹ is N or C-A¹ and A¹ and A² are each H are excluded.

In the preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl, phenanthrenyl, and is preferably in turn phenyl, hetaryl (synonymous with heteroaryl, including as part of a larger unit, for example hetarylalkyl) is selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl is a saturated 4-, 5- or 6-membered ring containing 1 or 2 nitrogen atoms and/or one oxygen atom and/or one sulphur atom, for example azetidinyl, azolidinyl, azinanyl, oxetanyl, oxolanyl, oxanyl, dioxanyl, thiethanyl, thiolanyl, thianyl, piperazinyl, morpholinyl and tetrahydrofuryl.

In the particularly preferred definitions, unless stated otherwise, halogen is selected from the group of fluorine, chlorine, bromine and iodine, preferably in turn from the group of fluorine, chlorine and bromine, aryl (including as part of a larger unit, for example arylalkyl) is selected from the group of phenyl, naphthyl, anthryl and phenanthrenyl, and is preferably in turn phenyl, hetaryl (including as part of a larger unit, for example hetarylalkyl) is selected from the group of pyridyl, pyrimidyl, pyrazanyl, thiazolyl, isothiazolyl and pyridazinyl and heterocyclyl is selected from the group of azetidinyl, azolidinyl, azinanyl, oxetanyl, oxolanyl, oxanyl, dioxanyl, thiethanyl, thiolanyl, thianyl and tetrahydrofuryl.

In the very particularly preferred definitions, unless stated otherwise, aryl is phenyl, hetaryl (synonymous with heteroaryl, including as part of a larger unit, for example hetarylalkyl) is pyridyl, pyrimidyl, pyrazanyl and pyridazinyl and heterocyclyl is tetrahydrofuryl and dioxanyl.

Halogen-substituted radicals, for example haloalkyl, are mono- or polyhalogenated, up to the maximum number of possible substituents. In the case of polyhalogenation, the halogen atoms may be the same or different. In this case, halogen is fluorine, chlorine, bromine or iodine, especially fluorine, chlorine or bromine.

Saturated or unsaturated hydrocarbyl radicals, such as alkyl or alkenyl, may in each case be straight-chain or branched as far as possible, including in combination with heteroatoms, as, for example, in alkoxy.

Unless stated otherwise, optionally substituted radicals may be mono- or polysubstituted, where the substituents in the case of polysubstitution may be the same or different.

The radical definitions or elucidations given above in general terms or within areas of preference apply to the end products and correspondingly to the starting materials and intermediates. These radical definitions can be combined with one another as desired, i.e. including combinations between the respective preferred ranges.

Preference is given in accordance with the invention to novel compounds of the formula (Ib) in which a combination of the definitions listed above as preferred is present.

Particular preference is given in accordance with the invention to novel compounds of the formula (Ib) in which a combination of the definitions listed above as particularly preferred is present.

Very particular preference is given in accordance with the invention to novel compounds of the formula (Ib) in which a combination of the definitions listed above as very particularly preferred is present.

Explicitly very particular preference is given in accordance with the invention to novel compounds of the formula (Ib) in which a combination of the definitions listed above as explicitly very particularly preferred is present.

In a particular group of compounds of the formula (I), the radicals are each defined as follows.

Het is the radical

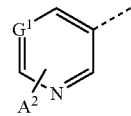

in which the dotted line represents the bond to one of the nitrogen atoms in the pyrazole ring.

$G^1$ is N or C-A¹.

$A^1$ is hydrogen.

$A^2$ is hydrogen.

$R^1$ is a radical from the group of methyl, ethyl, isopropyl, n-propyl, n-butyl, sec-butyl, tert-butyl, 2,2-dimethylpropyl, trifluoromethyl, 2,2,2-trifluoroethyl, 2,2-difluoroethyl, 2,2-difluoro-n-propyl, methylsulphanylmethyl, methylsulphanylethyl, methylsulphanyl-n-propyl, 1-(methylsulphanyl)propan-2-yl, methoxycarbonylmethyl, ethoxycarbonylmethyl, methoxycarbonylethyl, ethoxycarbonylethyl, dimethylaminocarbonylmethyl, diethylaminocarbonylmethyl, N-ethyl-N-methylaminocarbonylmethyl, N-isopropyl-N-methylaminocarbonylmethyl, dimethylaminocarbonylethyl, diethylaminocarbonylethyl, N-ethyl-N-methylaminocarbonylethyl, N-isopropyl-N-methylaminocarbonylethyl, N-cyclopropyl-N-methylaminocarbonylmethyl, N-cyclopropyl-N-methylaminocarbonylethyl, cyclopropyl, 1-cyanocyclopropyl, 1-chlorocyclopropyl, 1-fluorocyclopropyl, 2-cyanocyclopropyl, 2-chlorocyclopropyl, 2-fluorocyclopropyl, 2,2,3,3-tetrafluorocyclopropyl, cyclobutyl, cyclopentyl, cyclohexyl, 4-trifluoromethylcyclohexyl, cyclopropylmethyl, heterocyclylmethyl and heterocyclylethyl, in each case singly to triply, identically or differently halogen-substituted aryl, arylmethyl and arylethyl, hetarylmethyl and hetarylethyl, in which heterocyclyl is tetrahydrofuran-2-yl, hetaryl is pyrimidin-2-yl and pyridin-2-yl, and aryl is phenyl, 4-methylphenyl and 4-chlorophenyl.

$R^2$ is hydrogen.

Q is C—R³.

$R^3$ is a radical from the group of hydrogen, methyl, ethyl, isopropyl, tert-butyl and trifluoromethyl.

V is oxygen.

It has additionally been found that the novel compounds of the formula (I) can be prepared by the processes described below.

The compounds of the formula (Ia) and (Ib) can be prepared, for example, by process A in two steps, as shown in the scheme below. The aminopyrazoles of the formulae (IIIa) and (IIIb) required for that purpose can be prepared, for example, by processes B, C and D.

activation (cf. B. M. Trost and I. Fleming in Comprehensive Organic Synthesis, ed. Pergamon, 1991, vol. 6). Alternatively, the literature discloses activation methods by formation of an aluminium amide (see T. Ooi and K. Marouka in Science of Synthesis, ed. Georg Thieme, 2003, vol. 7, 225-246). These aluminium amides can be prepared, for example, from the amines or salts thereof by reaction with trimethylaluminium or the air-stable adduct thereof with

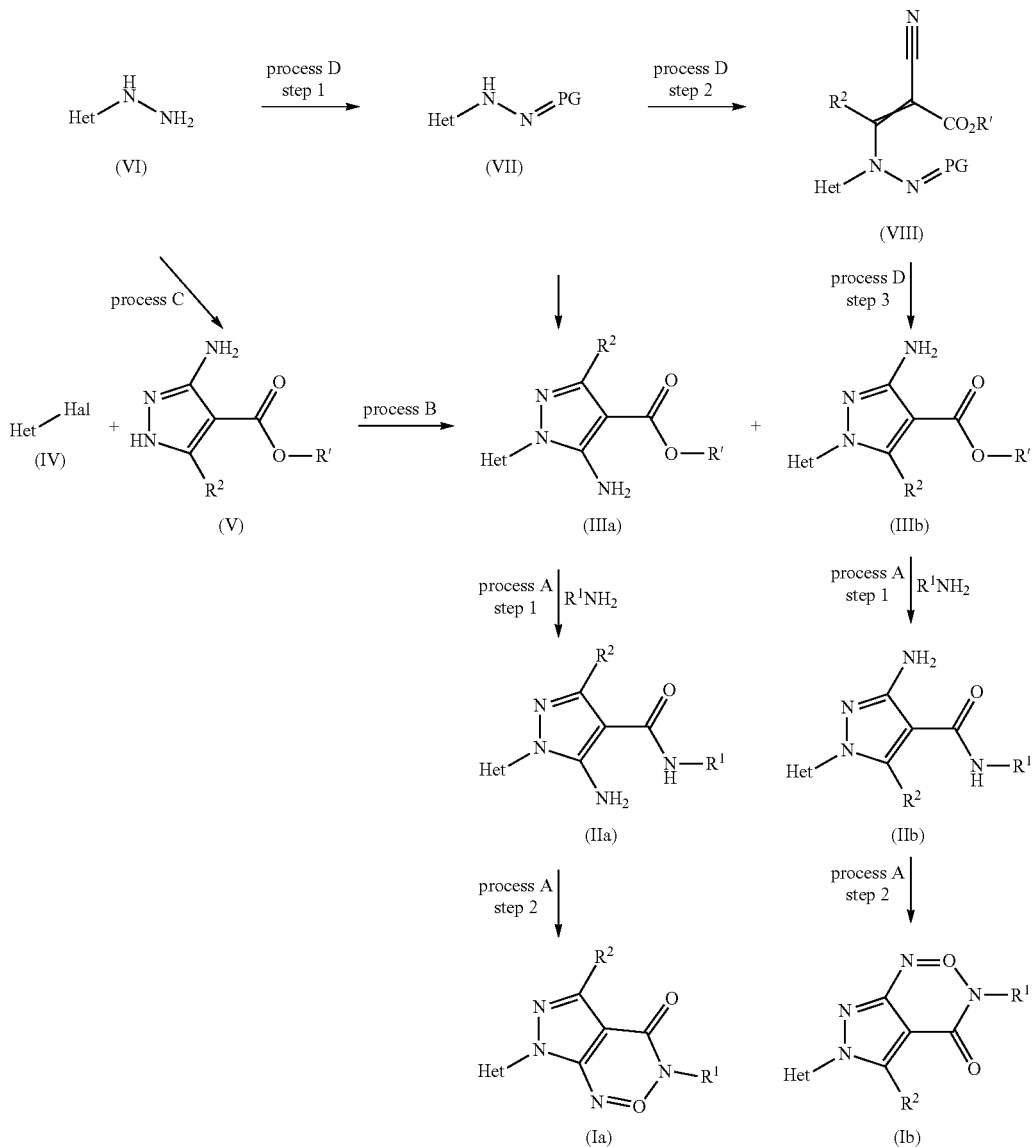

where Het, Q, $R^1$ and $R^2$ are each as defined above, R' is hydrogen or alkyl (especially methyl and ethyl), Hal is halogen (preferably chlorine, bromine and iodine) and PG is a suitable protecting group.

Process A

The compounds of the formulae (Ia) and (Ib) can be synthesized in two steps with the aid of methods known from the literature.

In the first synthesis step, compounds of the formulae (IIIa) and (IIIb) can be converted by various methods to carboxamides of the formulae (IIa) and (IIb) respectively. When R'=alkyl, this conversion can be effected without 1,4-diazobicyclo[2.2.2]octane (DABCO) (cf. S. Woodward in Tet. Lett. 2006, 47, 5767-5769).

Alternatively, the aminopyrazoles of the formulae (IIIa) and (IIIb), with R'=alkyl, can be converted in two stages to the amides of the formulae (IIa) and (IIb) respectively: first hydrolysis to the carboxylates, for example by reaction with an inorganic base (preferably sodium hydroxide and potassium hydroxide solutions), optionally in an inert organic solvent (it is optionally possible, by acidification with a dilute acid (e.g. aqueous hydrochloric acid), to prepare and isolate the carboxylic acids of the formulae (IIIa) and (IIIb) with R'=hydrogen); subsequent amidation reaction with the desired amines leads to the compounds of the formulae (IIa) and (IIb) respectively. For the amidation step, numerous reaction conditions have been described, for example G. Benz in Comprehensive Organic Synthesis, 1st ed., Pergamon Press, Oxford, 1991, vol. 6, p. 381-417; P. D. Bailey et al. in Comprehensive Organic Functional Group Transformation, 1st ed., Elsevier Science Ltd., Oxford, 1995, vol. 5, p. 257-308 and R. C. Larock in Comprehensive Organic Transformations, 2nd ed., Wiley-VCH, New York, Weinheim, 1999, p. 1929-1994. Some of these reactions proceed via intermediate carbonyl chlorides, which can be used in isolated form or having been generated in situ.

The amidation reactions are optionally effected in the presence of a condensing agent, optionally in the presence of an acid acceptor and optionally in the presence of a solvent.

Useful condensing agents are all the condensing agents typically usable for such amidation reactions. Examples include acid halide formers such as phosgene, phosphorus trichloride, oxalyl chloride or thionyl chloride; carbodiimides such as N,N'-dicyclohexylcarbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methoiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt) and 4-(4,6-dimethoxy-1,3,5-triazin-2-yl)-4-methylmorpholinium salt (DMT.MM), usually available as the chloride. These reagents can be used separately or, if appropriate, in combination.

Useful acid acceptors are all customary inorganic or organic bases, for example triethylamine, diisopropylethylamine, N-methylmorpholine or N,N-dimethylaminopyridine. Process A according to the invention is optionally carried out in the presence of a suitable reaction auxiliary, for example N,N-dimethylformamide or N,N-dimethylaminopyridine. Useful solvents or diluents include all inert organic solvents, for example aliphatic or aromatic hydrocarbons (such as petroleum ether, toluene), halogenated hydrocarbons (such as chlorotoluene, dichloromethane, chloroform, 1,2-dichloroethane), ethers (such as diethyl ether, dioxane, tetrahydrofuran, 1,2-dimethoxyethane), esters (such as ethyl or methyl acetate), nitrohydrocarbons (such as nitromethane, nitroethane, nitrobenzene), nitriles (such as acetonitrile, benzonitrile), amides (such as N,N-dimethylformamide, N,N-dimethylacetamide, N-methylformanilide, N-methylpyrrolidone, hexamethylphosphoramide), and also dimethyl sulphoxide or water or mixtures of the solvents mentioned.

It is also possible to use mixed anhydrides for preparation of compounds of the formula (III) (cf. J. Am. Chem. Soc. 1967, 5012). In this process, it is possible to use various chloroformic esters, for example isobutyl chloroformate and isopropyl chloroformate. It is likewise possible for this purpose to use diethylacetyl chloride, trimethylacetyl chloride and the like.

In a second synthesis step, the carboxamides of the formulae (IIa) and (IIb) can be cyclized to the compounds of the formulae (Ia) and (Ib) respectively.

In the case that Q=C—$R^3$ in which $R^3$ is H or alkyl, the cyclization of carboxamides of the formulae (IIa) and (IIb) can be performed with an orthoester, such as triethyl orthoformate or triethyl orthoacetate, optionally in the presence of a solvent or diluent (for example in the presence of alcohols such as ethanol, but also in the presence of N,N-dimethylformamide or N,N-dimethylacetamide), optionally in the presence of an organic acid (for example para-toluenesulphonic acid or acetic acid) or inorganic acid (for example hydrochloric acid or sulphuric acid) in catalytic or stoichiometric amounts or in excess. The acids mentioned can also be used in place of the solvent or diluent. In the case that $R^3$=H, there are examples of such reactions with triethyl orthoformate in Archiv der Pharmazie 2000, 333(8), 261-266 (for preparation of quinazolinones), J. Het. Chem. 1990, 27(7), 1953-1956 (idem.), WO2010/54398 (for preparation of pyrazinopyrimidinones). In the case that $R^3$=methyl, see, for example, WO2010/100189 (for preparation of quinazolinones).

In the case that Q=C—$R^3$ in which $R^3$ is alkyl or haloalkyl, the pyrazolopyrimidinones of the formulae (Ia) and (Ib) can also be prepared by reaction of the carboxamides of the formulae (IIa) and (IIb) respectively with appropriate carbonyl halides or carboxylic anhydrides by methods known from the literature, as described, for example, in WO2009/143049 in the case that $R^3$=methyl and in WO 2008/039489 in the case that $R^3$=trifluoromethyl.

In the case that Q=N, the pyrazolopyrimidinones of the formulae (Ia) and (Ib) can be prepared by azo diazotization of the carboxamides of the formulae (IIa) and (IIb) respectively, by methods known from the literature. For example, compounds of the formulae (IIa) and (IIb) are admixed at 0 to 5° C. with a nitrite source, such as sodium nitrite or isobutyl nitrite, typically in water, alcohol or a polar inert solvent, and in the presence of an organic or inorganic acid. Examples of reaction conditions can be found in WO 2004/242572 or in J. Chem. Soc. Perkin Trans. 1, 1980, 633-638.

The aminopyrazoles of the formulae (IIIa) and (IIIb) required in process A can be prepared, for example, by processes B, C and D.

Process B

Aminopyrazoles of the formulae (IIIa) and (IIIb) can be prepared in one step, for example by means of an Ullmann reaction, by methods known in principle (cf. Chem. Rev. 2008, 108, 3054-3131) from the corresponding bromides of the formula (IV) and the aminopyrazoles of the formula (V).

Examples of the arylation of aminopyrazoles are described in WO2007/039146. For reactions of this kind, for example, catalysts based on copper(I) (e.g. copper(I) iodide) are utilized, in the presence of a base (e.g. potassium carbonate), and of a ligand (e.g. trans-1,2-diaminocyclohexane or trans-N,N'-dimethyl-1,2-cyclohexanediamine) or of a combination thereof, in a suitable solvent (e.g. dioxane, N,N-dimethylformamide, N,N-dimethylacetamide or pyridine) or of a combination of solvents. Temperatures between 80 and 180° C. are usually required for the reaction.

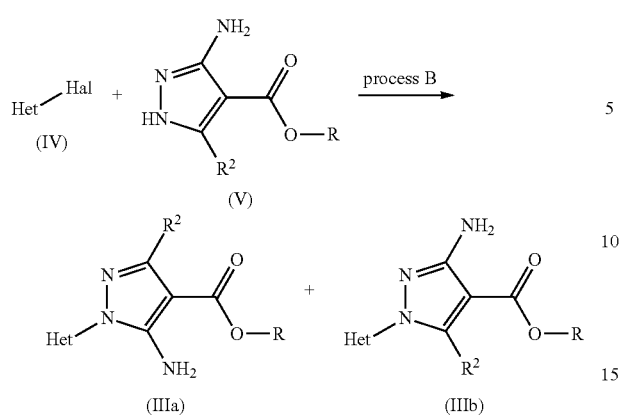

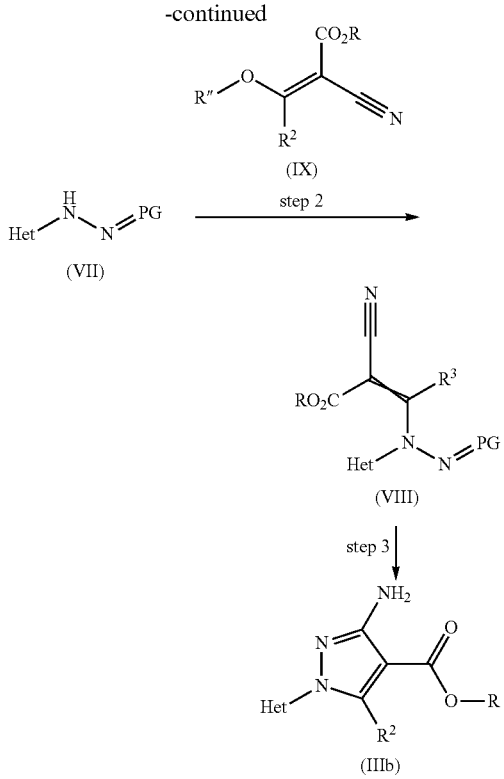

In the performance of process B according to the invention, it is possible to use any commercial microwave apparatus suitable for these reactions (e.g. Anton Paar Monowave 300, CEM Discover S, Biotage Initiator 60).

The aminopyrazoles of the formulae (IIIa) and (IIIb) prepared in this way can be separated, for example by means of chromatographic separation using silica gel or RP(C-18), or by stirring or recrystallization using suitable solvents.

Process C

Alternatively, aminopyrazoles of the formula (IIIa) can be prepared by methods known in principle from hydrazines of the formula (VI) or salts thereof (preference being given to hydrochlorides). For example according to Robins' syntheses in J. Amer. Chem. Soc. 1956, 78, 784-790 or according to J. Med. Chem. 2005, 48, 5162-5174, by reacting them at a temperature between 50° C. and 100° C. with a suitable cyano compound of the formula (IX) in which R and R" are alkyl (preferably methyl and ethyl), optionally in an inert organic solvent (e.g. alcohols).

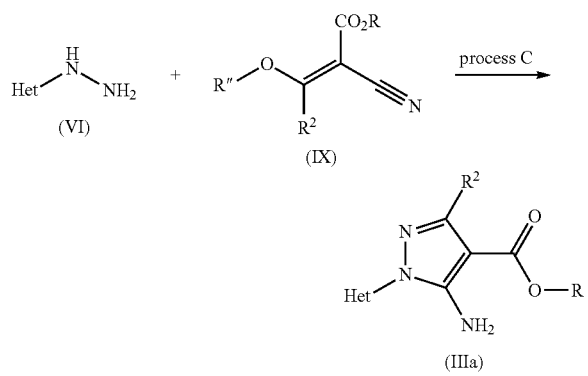

Process D

As an alternative to process B, aminopyrazoles of the formula (IIIb) can be prepared by methods known from the literature from hydrazines of the formula (VI) or salts thereof (preferably hydrochlorides) (cf. E. J. Med. Chem. 2011, 46, 3867-3876).

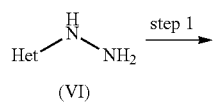

In step 1, the hydrazine of the formula (VI) is protected, for example by reaction with an aldehyde (typically benzaldehyde, cf. Biorg. Med. Chem. Let 2004, 14, 4585-4589), to form a hydrazone. The protected compound of the formula (VII) can be reacted with a cyano derivative of the formula (IX) to give compounds of the formula (VIII) (cf. J. Het. Chem. 1990, 27, 1805-1807), typically in an inert organic solvent (for example an alcohol) at a temperature between 50° C. and 100° C. (step 2). Subsequent reaction of compounds of the formula (VIII) with an acid (e.g. hydrochloric acid) leads to the aminopyrazole of the formula (IIIb) (step 3).

Halides of the formula (IV) (preferably chlorides, bromides and iodides) are commercially available and can be synthesized by methods known from the literature; cf., for example, Y. Yamamoto, Heterocycles 1981, 16 (7), 1161-1164, for 3-iodopyridine (Hal=iodine); S. M. E. Englert, J. Amer. Chem. Soc. 1929, 51(3), 863-866, for 3-bromopyridine (Hal=bromine); D. E. Pearson, J. Org. Chem. 1961, 26, 789-792, and for 3-chloropyridine (Hal=chlorine); WO 2006/074884 for 3-bromo-5-fluoropyridine and M. Schlosser, Eur. J. Org. Chem. 2002, 24, 4174-4180, for 3-fluoro-5-iodopyridine; D. Kikelj, U. Urleb, Science of Synthesis 2002, 11, 627-833, for 5-iodothiazole (Hal=iodine) and WO 2008/057336 for 5-bromothiazole (Hal=bromine); D. W. Brown, M. Sainsbury, Science of Synthesis 2002, 11, 507-572, for 4-iodoisothiazole (Hal=iodine), I. F. Huebenett et al., Angew. Chem. 1963, 75 (24), 1189-1193, for 4-bromoisothiazole (Hal=bromine) or 4-chloroisothiazole (Hal=chlorine); WO 2010/083283 for 4-iodo-1H-pyrazole (Hal=iodine), WO2010/018481 for 4-bromo-1H-pyrazole (Hal=bromine); WO 2001/034137 for 4-iodo-1-methyl-1H-pyrazole (Hal=iodine), WO 93/21186 for 4-bromo-1-methyl-1H-pyrazole (Hal=bromine); WO 2010/090290 for 1-cyclopropyl-4-iodo-1H-pyrazole (Hal=iodine), WO 2008/088692 for 1-(difluoromethyl)-4- iodo-1H-pyrazole and 4-iodo-(1,1,2,2-tetrafluoroethyl)-1H-pyrazole (Hal=iodine); A. Seggio et al., J. Org. Chem. 2007, 72 (17), 6602-6605, for 4-iodopyridazine (Hal=iodine) and JP 63250385 for 4-bromopyridazine (Hal=bromine).

Heterocyclic hydrazines of the formula (VI) are commercially available or can be prepared by methods known from the literature from the corresponding halides of the formula (IV), as described, for example, in WO 2010/015849 for various heterocycles: by reaction with hydrazine hydrate, optionally in an inert organic solvent (e.g. ethanol), at temperatures between 60 and 120° C.; or by reaction with di-tert-butyl hydrazodicarboxylate and subsequent cleavage of the tert-butyl carboxylate groups by addition of an acid (typically hydrochloric acid in an organic solvent, for example dioxane; also with trifluoroacetic acid), which leads to the formation of the corresponding salts.

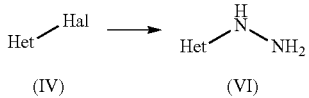

The following hydrazines of the formula (VI), for example, are commercially available: 3-hydrazinylpyridine, 5-hydrazinylpyrimidine, 4-hydrazinylpyridazine.

Cyano compounds of the formula (IX) can be prepared from alkyl cyanoacetates (preferably methyl and ethyl cyanoacetate) by methods known from the literature.

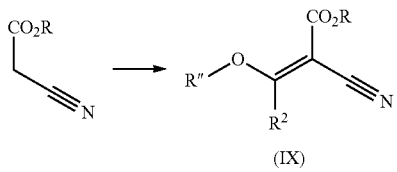

Commercially available examples include ethyl 2-cyano-3-ethoxyacrylate (R=R''=ethyl; $R^2$=hydrogen), ethyl 2-cyano-3-ethoxybut-2-enoate—also called ethyl 2-cyano-3-ethoxycrotonate—(R=R''=ethyl; $R^2$=methyl), ethyl (2E)-2-cyano-3-ethoxypent-2-enoate (R=R''=$R^2$=ethyl). For other alkyl groups, the synthesis of the cyano compounds of the formula (IX) can be performed by the method described in J. Amer. Chem. Soc. 1956, 75, 5294-5299. This involves the reaction of the corresponding orthoesters (e.g. triethyl orthopropionate in the case that $R^2$=propyl) with an alkyl cyanoacetate at relatively high temperatures.

Process E

N-Substituted pyrazolopyrimidinones of the formula (I) with Q=C—$R^3$ in which $R^3$ is H or alkyl can also be prepared in two steps from the aminopyrazoles of the formula (III), as shown in the schemes below.

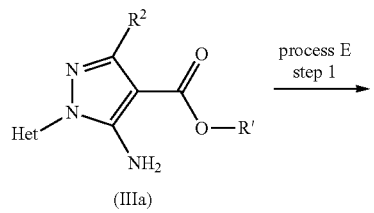

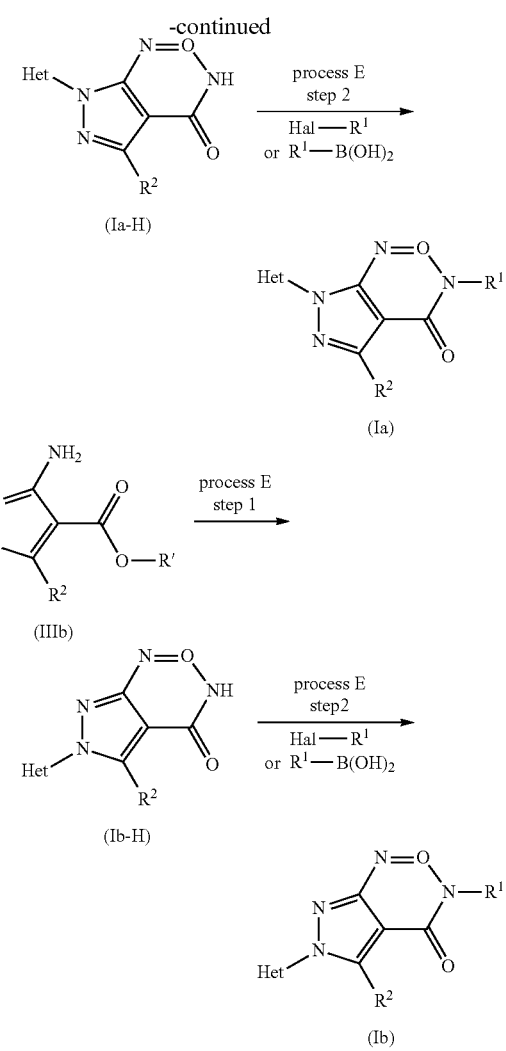

The conversion of the aminopyrazoles of the formulae (IIIa) and (IIIb) to pyrazolopyrimidinones of the formulae (Ia-H) and (Ib-H) respectively by reaction with formamidine acetate in methoxyethanol under reflux overnight is known in the literature in the case that Q=C—H; cf. US 2007/0281949.

The N-substitution of the pyrazolopyrimidinones of the formulae (Ia-H) and (Ib-H) can be effected in different ways. The literature discloses N-arylations (in the case that $R^1$=aryl, hetaryl) of pyrimidinones by $S_NAr$ reaction with a suitable aryl substrate, for example aryl fluorides activated by nitro, nitrile or trifluoromethyl groups in the presence of a base and of an inert organic solvent; cf. examples in DE 4431218. For different aryl and hetaryl compounds, the reaction takes place preferably under transition metal catalysis or mediation. Numerous illustrative reaction conditions are described in the literature, for example in WO2007/146824. Preference is given to using copper or copper salts, for example copper(I) iodide, copper(I) oxide, copper(I) triflate or copper(II) triflate, as catalyst, frequently in the presence of ligands, for example diamine ligands such as N,N'-dimethylethylenediamine, N,N-dimethylethylenediamine or trans-N,N'-dimethyl-1,2-cyclohexanediamine. A review can be found in Chem. Sci. 2010, vol. 1, 13-31. Alternatively, it is possible to use 1,3-diketones, for example 2,4-pentanedione, 2,2,6,6-tetramethyl-3,5-heptanedione or dibenzoylmethane, amino acids, for example L-proline or glycine, or other compounds such as 8-hydroxyquinoline (Tetrahedron Lett. 2009, vol. 50, 7293-7296), dibenzylideneacetone, bipyridine or phenanthroline. In general, the reaction is performed in the presence of a base, frequently carbonate or phosphate bases, for example potassium carbonate, sodium carbonate, caesium carbonate or potassium phosphate, in suitable solvents, for example dioxane, toluene, dimethyl sulphoxide or N,N-dimethylformamide. It is also possible to use other additives, for example potassium iodide, caesium fluoride or other salts.

Alternatively, it is possible to perform reactions of this kind under palladium catalysis, for instance using catalysts such as palladium acetate, tetrakis(triphenylphosphine)palladium, bis(triphenylphosphine)palladium(II) chloride, tris(dibenzylideneacetone)dipalladium(0) in the presence of ligands, for example 2,2'-bis(diphenylphosphino)-1,1'-binaphthyl, 9,9-dimethyl-4,5-bis(diphenylphosphino)xanthene, 1,1'-bis(diphenylphosphino)ferrocene, and bases, for example potassium carbonate, sodium carbonate, caesium carbonate or potassium phosphate, in suitable solvents, for example dioxane, toluene, dimethyl sulphoxide or N,N-dimethylformamide.

In general, compounds of the formulae (Ia) and (Ib) can alternatively be prepared by reaction of suitable boronic acids with the pyrazolopyrimidinones of the formulae (Ia-H) and (Ib-H) respectively. In general, the reactions take place under catalysis or mediation by copper(II) salts, for example copper(II) acetate, copper(II) triflate, or else by copper(I) salts, for example copper(I) chloride, copper(I) acetate, under an air or oxygen atmosphere, frequently under dehydrating conditions (for example in the presence of molecular sieve). Bases used are, for example, triethylamine, N-ethyldiisopropylamine, pyridine, 2,6-lutidine, N-methylmorpholine or 1,8-diazabicycloundec-7-ene in suitable solvents, for example dichloromethane, dichloroethane, methanol, N,N-dimethylformamide, tetrahydrofuran, dioxane, acetonitrile, ethyl acetate or toluene. The literature describes numerous examples, including WO 2008/062905 or WO 2009/133970, which describe pyrimidinones. Comprehensive reviews can be found in Synthesis 2011, no. 6, 829-856 or in Tetrahedron 2012, vol. 68, 7735-7754. Instead of the boronic acid, it is also possible to use other boron compounds, for instance potassium trifluoroborate, boronic esters, etc., or else other organometallic compounds, for instance stannanes, silanes or bismuthanes.

Finally, it has been found that the novel compounds of the formula (I) have very pronounced biological properties and are suitable in particular for controlling animal pests, especially insects, arachnids and nematodes, which are encountered in agriculture, in forests, in the protection of stored products and materials and in the hygiene sector.

The inventive active ingredients, given good plant tolerance, favourable homeotherm toxicity and good environmental compatibility, are suitable for protecting plants and plant organs, for increasing harvest yields, for improving the quality of the harvested material and for controlling animal pests, especially insects, arachnids, helminths, nematodes and molluscs, which are encountered in agriculture, in horticulture, in animal husbandry, in forests, in gardens and leisure facilities, in the protection of stored products and of materials, and in the hygiene sector. They can be used with preference as crop protection agents. They are effective against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus.*

From the order of the Dermaptera, for example, *Forficula auricularia.*

From the order of the Diplopoda, for example, *Blaniulus guttulatus.*

From the order of the Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echi-*

*nococcus multilocularis, Enterobius vermicularis, Faciola* spp., *Haemonchus* spp., *Heterakis* spp., *Hymenolepis nana, Hyostrongulus* spp., *Loa loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella pseudospiralis, Trichostrongulus* spp., *Trichuris trichiura, Wuchereria bancrofti.*

It is also possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare, Oniscus asellus* and *Porcellio scaber.*

From the order of the Isoptera, for example, *Reticulitermes* spp. and *Odontotermes* spp.

From the order of the Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example, *Ceratophyllus* spp., *Xenopsylla cheopis.*

From the order of the Symphyla, for example, *Scutigerella immaculata.*

From the order of the Thysanoptera, for example, *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni* and *Thrips* spp.

From the order of the Thysanura, for example, *Lepisma saccharina.*

The phytoparasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans* and *Xiphinema* spp.

The inventive compounds can, at particular concentrations or application rates, also be used as herbicides, safeners, growth regulators or agents to improve plant properties, or as microbicides, for example as fungicides, antimycotics, bactericides, viricides (including compositions against viroids) or as compositions against MLO (*Mycoplasma*-like organisms) and RLO (*Rickettsia*-like organisms). They can also be used as intermediates or precursors for the synthesis of other active ingredients.

The active ingredients can be converted to the customary formulations, such as solutions, emulsions, wettable powders, water- and oil-based suspensions, powders, dusts, pastes, soluble powders, soluble granules, granules for broadcasting, suspoemulsion concentrates, natural compounds impregnated with active ingredient, synthetic substances impregnated with active ingredient, fertilizers and also microencapsulations in polymeric substances.

These formulations are produced in a known manner, for example by mixing the active ingredients with extenders, i.e. liquid solvents, and/or solid carriers, optionally with use of surfactants, i.e. emulsifiers and/or dispersants, and/or foam formers. The formulations are produced either in suitable production plants or else before or during application.

Auxiliaries used may be those substances which are suitable for imparting particular properties to the composition itself or and/or to preparations derived therefrom (for example spray liquors, seed dressings), such as certain technical properties and/or also particular biological properties. Typical auxiliaries include: extenders, solvents and carriers.

Suitable extenders are, for example, water, polar and nonpolar organic chemical liquids, for example from the classes of the aromatic and nonaromatic hydrocarbons (such as paraffins, alkylbenzenes, alkylnaphthalenes, chlorobenzenes), the alcohols and polyols (which may optionally also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to use, for example, organic solvents as auxiliary solvents. Useful liquid solvents essentially include: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl sulphoxide, and also water.

Useful solid carriers include:
for example ammonium salts and natural rock flours, such as kaolins, aluminas, talc, chalk, quartz, attapulgite, montmorillonite or diatomaceous earth, and synthetic rock flours, such as finely divided silica, alumina and silicates; useful solid carriers for granules include: for example, crushed and fractionated natural rocks such as calcite, marble, pumice, sepiolite and dolomite, and also synthetic granules of inorganic and organic flours, and granules of organic material such as paper, sawdust, coconut shells, maize cobs and tobacco stalks; useful emulsifiers and/or foam formers include: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; useful dispersants include nonionic and/or ionic substances, for example from the classes of the alcohol-POE and/or -POP ethers, acid and/or POP POE esters, alkylaryl and/or POP POE ethers, fat and/or POP POE adducts, POE- and/or POP-polyol derivatives, POE- and/or POP-sorbitan or -sugar adducts, alkyl or aryl sulphates, alkyl- or arylsulphonates and alkyl or aryl phosphates or the corresponding PO-ether adducts. Additionally suitable are oligo- or polymers, for example those derived from vinylic monomers, from acrylic acid, from EO and/or PO alone or in combination with, for example, (poly)alcohols or (poly) amines. It is also possible to use lignin and its sulphonic acid derivatives, unmodified and modified celluloses, aromatic and/or aliphatic sulphonic acids and also their adducts with formaldehyde.

In the formulations it is possible to use tackifiers such as carboxymethyl cellulose, natural and synthetic polymers in the form of powders, granules or latices, such as gum arabic, polyvinyl alcohol and polyvinyl acetate, or else natural phospholipids such as cephalins and lecithins and synthetic phospholipids.

It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

Further additives may be perfumes, mineral or vegetable, optionally modified oils, waxes and nutrients (including trace nutrients), such as salts of iron, manganese, boron, copper, cobalt, molybdenum and zinc.

Additional components may be stabilizers, such as cold stabilizers, preservatives, antioxidants, light stabilizers, or other agents which improve chemical and/or physical stability.

The formulations contain generally between 0.01 and 98% by weight of active ingredient, preferably between 0.5 and 90%.

The inventive active ingredients may be used as such or in formulations thereof, including in a mixture with one or more suitable fungicides, bactericides, acaricides, nematicides, insecticides, microbicides, fertilizers, attractants, sterilants, synergists, safeners, semiochemicals and/or plant growth regulators, in order thus, for example, to broaden the spectrum of action, to prolong the duration of action, to increase the rate of action, to prevent repulsion or prevent evolution of resistance. In addition, combinations of this kind can improve plant growth, increase tolerance to high or low temperatures, to drought or to increased levels of water and/or soil salinity, improve flowering performance, facilitate harvesting and increase yields, accelerate ripening, increase the quality and/or nutritional value of the harvested products, prolong storage life and/or improve the processibility of the harvested products. In general, by combining the inventive active ingredients and mixing partners, synergistic effects are obtained, meaning that the efficacy of the mixture in question is greater than the efficacy of the individual components. In general, the combinations can be used either as seed treatments or else in premixes, tankmixes or readymixes.

Particularly favourable mixing partners are, for example, the following:

Insecticides/Acaricides/Nematicides:

The active ingredients identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example organochlorines, for example chlordane and endosulfan (alpha-); or
fiproles (phenylpyrazoles), for example ethiprole, fipronil, pyrafluprole and pyriprole.
(3) Sodium channel modulators/voltage-dependent sodium channel blockers, for example
pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, eto-fenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; or
DDT; or methoxychlor.
(4) Nicotinergic acetylcholine receptor agonists, for example
neonicotinoids, for example acetamiprid, clothianidin, dinotefuran, imidacloprid, nitenpyram, thiacloprid, thiamethoxam; or
nicotine.
(5) Allosteric acetylcholine receptor modulators (agonists), for example
spinosyns, for example spinetoram and spinosad.
(6) Chloride channel activators, for example
avermectins/milbemycins, for example abamectin, emamectin benzoate, lepimectin and milbemectin.
(7) Juvenile hormone analogues, for example hydroprene, kinoprene, methoprene; or fenoxycarb; pyriproxyfen.
(8) Active ingredients with unknown or nonspecific mechanisms of action, for example
fumigants, for example methyl bromide and other alkyl halides; or
chloropicrin; sulphuryl fluoride; borax; tartar emetic.
(9) Selective antifeedants, for example pymetrozine; or flonicamid.
(10) Mite growth inhibitors, for example clofentezine, diflovidazin, hexythiazox, etoxazole.
(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins, for example Cry1Ab, Cry1Ac, Cry1Fa, Cry2Ab, mCry3A, Cry3Ab, Cry3Bb, Cry34/35Ab1.
(12) Oxidative phosphorylation inhibitors, ATP disruptors, for example diafenthiuron; or
organotin compounds, for example azocyclotin, cyhexatin, fenbutatin oxide; or
propargite; tetradifon.
(13) Oxidative phosphorylation decouplers that disrupt the H proton gradient, for example, chlorfenapyr and DNOC.
(14) Nicotinergic acetylcholine receptor antagonists, for example bensultap, cartap (hydrochloride), thiocylam, and thiosultap (sodium).
(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.
(16) Chitin biosynthesis inhibitors, type 1, for example buprofezin.
(17) Moulting disruptors, for example cyromazine.
(18) Ecdysone agonists/disruptors, for example
diacylhydrazines, for example chromafenozide, halofenozide, methoxyfenozide and tebufenozide.
(19) Octopaminergic agonists, for example amitraz.
(20) Complex-III electron transport inhibitors, for example hydramethylnone; acequinocyl; fluacrypyrim.
(21) Complex-I electron transport inhibitors, for example from the group of the METI acaricides, for example fenazaquin, fenpyroximate, pyrimidifen, pyridaben, tebufenpyrad, tolfenpyrad; or
rotenone (Derris).
(22) Voltage-dependent sodium channel blockers, for example indoxacarb; metaflumizone.
(23) Inhibitors of acetyl-CoA carboxylase, for example tetronic acid derivatives, for example spirodiclofen and spiromesifen; or tetramic acid derivatives, for example spirotetramat.
(24) Complex-IV electron transport inhibitors, for example phosphines, for example aluminium phosphide, calcium phosphide, phosphine, zinc phosphide; or cyanide.
(25) Complex-II electron transport inhibitors, for example cyenopyrafen.
(28) Ryanodine receptor effectors, for example diamides, for example flubendiamide, chlorantraniliprole (Rynaxypyr), cyantraniliprole (Cyazypyr) and also 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) or methyl 2-[3,5-dibromo-2-({[3-bromo-1-(3-chloropyridin-2-yl)-1H-pyrazol-5-yl]carbonyl}amino)benzoyl]-1,2-dimethylhydrazinecarboxylate (known from WO2007/043677).

Further active ingredients with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (1-1582, BioNeem, Votivo) and the following known active compounds:
4-{[(6-bromopyrid-3-yl)methyl](2-fluoroethyl) amino}furan-2(5H)-one (known from WO 2007/115644),
4-{[(6-fluoropyrid-3-yl)methyl](2,2-difluoroethyl) amino}furan-2(5H)-one (known from WO 2007/115644),
4-{[(2-chloro-1,3-thiazol-5-yl)methyl](2-fluoroethyl) amino}furan-2(5H)-one (known from WO 2007/115644),
4-{[(6-chloropyrid-3-yl)methyl](2-fluoroethyl) amino}furan-2(5H)-one (known from WO 2007/115644),
4-{[(6-chloropyrid-3-yl)methyl](2,2-difluoroethyl) amino}furan-2(5H)-one (known from WO 2007/115644),
4-{[(6-chloro-5-fluoropyrid-3-yl)methyl](methyl) amino}furan-2(5H)-one (known from WO 2007/115643),
4-{[(5,6-dichloropyrid-3-yl)methyl](2-fluoroethyl) amino}furan-2(5H)-one (known from WO 2007/115646),
4-{[(6-chloro-5-fluoropyrid-3-yl)methyl](cyclopropyl) amino}furan-2(5H)-one (known from WO 2007/115643),
4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [1-(6-chloropyridin-3-yl)ethyl](methyl)oxido-$\lambda^4$-sulphanylidenecyanamide (known from WO 2007/149134) and its diastereomers {[(1R)-1-(6-chloropyridin-3-yl)ethyl](methyl)oxido-lambda$^6$-sulphanylidene}cyanamide (A) and {[(1S)-1-(6-chloropyridin-3-yl)ethyl](methyl)oxido-lambda$^6$-sulphanylidene}cyanamide (B) (likewise known from WO 2007/149134) and sulfoxaflor (likewise known from WO 2007/149134) and its diastereomers {(R)-1-[6-(trifluoromethyl)pyridin-3-yl]ethyl}-(R)-(methyl)oxido-lambda$^4$-sulphanylidenecyanamide (A$^1$) and {(S)-1-[6-(trifluoromethyl)pyridin-3-yl]ethyl}-(S)-(methyl)oxido-lambda$^4$-sulphanylidenecyanamide (A$^2$), referred to as diastereomer group A (known from WO 2010/074747, WO 2010/074751), {(R)-1-[6-(trifluoromethyl)pyridin-3-yl]ethyl}-(S)-(methyl)oxido-lambda$^4$-sulphanylidenecyanamide (B$^1$) and {(S)-1-[6-(trifluoromethyl)pyridin-3-yl]ethyl}-(R)-(methyl)oxido-lambda$^4$-sulphanylidenecyanamide (B$^2$), referred to as diastereomer group B (likewise known from WO 2010/074747, WO 2010/074751), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), 1-[2-fluoro-4-methyl-5-[(2,2,2-trifluoroethyl)sulphinyl]phenyl]-3-(trifluoromethyl)-1H-1,2,4-triazole-5-amines (known from WO 2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO 2006/129714), 2-cyano-3-(difluoromethoxy)-N,N-dimethylbenzenesulphonamide (known from WO2006/056433), 2-cyano-3-(difluoromethoxy)-N-methylbenzenesulphonamide (known from WO2006/100288), 2-cyano-3-(difluoromethoxy)-N-ethylbenzenesulphonamide (known from WO2005/035486), 4-(difluoromethoxy)-N-ethyl-N-methyl-1,2-benzothiazole-3-amine 1,1-dioxide (known from WO2007/057407) and N-[1-(2,3-dimethylphenyl)-2-(3,5-dimethylphenyl)ethyl]-4,5-dihydro-1,3-thiazole-2-amine (known from WO2008/104503).

In a preferred embodiment of the invention, a penetrant is additionally added to the crop protection compositions to enhance the action. Useful penetrants also include, for example, substances which promote the availability of the compounds of the formula (I) in the spray coating. These include, for example, mineral and vegetable oils. Useful oils include all mineral or vegetable oils—modified or otherwise—which are typically usable in agrochemical compositions. Examples include sunflower oil, rapeseed oil, olive oil, castor oil, colza oil, cornseed oil, cottonseed oil and soybean oil or the esters of the oils mentioned. Preference is given to rapeseed oil, sunflower oil and their methyl or ethyl esters, especially rapeseed oil methyl ester.

The concentration of penetrant in the inventive compositions can be varied within a wide range. In the case of a formulated crop protection composition, it is generally 1 to 95% by weight, preferably 1 to 55% by weight, particularly preferably 15-40% by weight. In the ready-to-use compositions (spray liquors), the concentrations are generally between 0.1 and 10 g/l, preferably between 0.5 and 5 g/l.

When used as insecticides, the inventive active ingredients may also be present in their commercially available formulations and in the use forms, prepared from these formulations, as a mixture with synergists. Synergists are compounds which enhance the action of the active ingredients, without any need for the synergist added to be active itself.

When used as insecticides, the inventive active ingredients may also be present in their commercially available formulations and in the use forms, prepared from these formulations, as a mixture with inhibitors which reduce degradation of the active ingredient after use in the environment of the plant, on the surface of parts of plants or in plant tissues.

The active ingredient content of the use forms prepared from the commercially available formulations may vary within wide limits. The active ingredient concentration of the use forms may be from 0.00000001 to 95% by weight of active ingredient, preferably between 0.00001 and 1% by weight.

The compounds are applied in a customary manner appropriate for the use forms.

All plants and parts of plants can be treated in accordance with the invention. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Examples include the important crop plants, such as cereals (wheat, rice), maize, soya, potatoes, sugarbeet, tomatoes, peas and other vegetable species, cotton, tobacco, oilseed rape and also fruit plants (the fruits produced being apples, pears, citrus fruits and grapes). Parts of plants shall be understood to mean all above-ground and below-ground parts and organs of plants, such as shoot, leaf, flower and root, examples including leaves, needles, stems, trunks, flowers, fruit bodies, fruits and seeds, and also roots, tubers and rhizomes. Parts of plants also include harvested material and vegetative and generative propagation material, for example cuttings, tubers, rhizomes, slips and seed.

The inventive treatment of the plants and plant parts with the active ingredients is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The terms "parts" or "parts of plants" or "plant parts" have been explained above.

More preferably, plants of the plant cultivars which are commercially available or are in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the treatment according to the invention may also result in superadditive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, increased flowering performance, easier harvesting, accelerated ripening, higher yields, higher quality and/or higher nutrient value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants which may be mentioned are the important crop plants, such as cereals (wheat, rice), maize, soya beans, potatoes, sugar beet, tomatoes, peas and other types of vegetable, cotton, tobacco, oilseed rape and also fruit plants (the fruits produced being apples, pears, citrus fruits and grapes), with particular emphasis being given to maize, soya beans, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors, and also resistance genes and correspondingly expressed proteins and toxins. Traits that are additionally particularly emphasized are the increased tolerance of the plants to certain active herbicidal compounds, for example imidazolinones, sulphonylureas, glyphosates or phosphinothricin (for example the "PAT" gene). The genes which impart the desired traits in question may also be present in combinations with one another in the transgenic plants. Examples of Bt plants include maize varieties, cotton varieties, soya bean varieties and potato varieties that are sold under the commercial names YIELD GARD® (e.g. maize, cotton, soya beans), KnockOut® (e.g. maize), StarLink® (e.g. maize), Bollgard® (cotton), Nucotn® (cotton) and NewLeafC (potatoes). Examples of herbicide-tolerant plants include maize varieties, cotton varieties and soya bean varieties which are sold under the commercial names Roundup Ready® (tolerance to glyphosate e.g. maize, cotton, soya beans), Liberty Link® (tolerance to phosphinothricin, e.g. oilseed rape), IMI® (tolerance to imidazolinones) and STS® (tolerance to sulphonylureas, e.g. maize). Herbicide-resistant plants (bred conventionally for herbicide tolerance) also include the varieties sold under the Clearfield® name (e.g. maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the inventive active ingredient mixtures. The areas of preference stated above for the active ingredients or mixtures also apply to the treatment of these plants. Particular emphasis is given to the treatment of plants with the compounds or mixtures specifically mentioned in the present text.

The control of animal pests by the treatment of the seed of plants has long been known and is the subject of constant improvement. Nevertheless, the treatment of seed gives rise to a series of problems which cannot always be solved in a satisfactory manner. Thus, it is desirable to develop methods for protecting the seed and the germinating plant which dispense with, or at least reduce considerably, the additional application of crop protection compositions during storage, after sowing or after emergence of the plants. It is additionally desirable to optimize the amount of active ingredient used so as to provide optimum protection for the seed and the germinating plant from attack by animal pests, but without damage to the plant itself by the active ingredient used. More particularly, methods for the treatment of seed should also take account of the intrinsic insecticidal or nematicidal properties of pest-resistant or -tolerant transgenic plants, in order to achieve optimum protection of the seed and of the germinating plant with minimum expenditure of crop protection products.

The present invention therefore also relates, more particularly, to a method for protection of seed and germinating plants from attack by pests, by treating the seed with a compound of the formula (I). The method of the invention for protection of seed and germinating plants against attack by pests comprises a method in which the seed is treated simultaneously in one operation with an active ingredient of the formula (I) and one or more mixing partners. It also comprises a method in which the seed is treated at different times with an active ingredient of the formula (I) and one or more mixing partners.

The invention likewise relates to the use of compounds of the formula (I) for treatment of seed for protecting the seed and the resulting plant from animal pests.

The invention further relates to seed which has been treated with a compound of the formula (I) for protection from animal pests. The invention also relates to seed which has been treated simultaneously with an active ingredient of the formula (I) and one or more mixing partners. The invention further relates to seed which has been treated at different times with an active ingredient of the formula (I) and one or more mixing partners. In the case of seed which has been treated at different times with an active ingredient of the formula (I) and one or more mixing partners, the individual active ingredients in the inventive composition may be present on the seed in different layers. In this case, the layers comprising an active ingredient of the formula (I) and the mixing partner(s) may be separated by an intermediate layer. The invention also relates to seed in which an active ingredient of the formula (I) and the mixing partner(s) have been applied as part of a coating or as a further layer or further layers in addition to a coating.

The invention further relates to seed which, after the treatment with a compound of the formula (I), is subjected to a film-coating process to prevent dust abrasion on the seed.

One of the advantages of the present invention is that the particular systemic properties of the inventive compositions mean that treatment of the seed with these compositions protects not only the seed itself but also the resulting plants after emergence from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

It should also be mentioned that compounds of the formula (I) can be used in combination with signalling technology compositions, leading, for example, to better colonization by symbionts, for example rhizobia, mycorrhizae and/or endophytic bacteria, and/or to optimized nitrogen fixation.

The inventive compositions are suitable for protection of seed of any plant variety which is used in agriculture, in the greenhouse, in forests or in horticulture. In particular, this is the seed of cereals (for example wheat, barley, rye, millet and oats), corn, cotton, soya beans, rice, potatoes, sunflowers, coffee, tobacco, canola, oilseed rape, beets (for example sugar beets and fodder beets), peanuts, vegetables (for example tomatoes, cucumbers, bean, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. In this context, the heterologous genes in transgenic seed may be derived from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, a compound of the formula (I) is applied to the seed alone or in a suitable formulation. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, has been treated, for example, with water and then dried again.

In general, in the treatment of the seed, it has to be ensured that the amount of the inventive composition and/or further additives applied to the seed is selected such that the germination of the seed is not impaired and the plant which arises therefrom is not damaged. This should be ensured particularly in the case of active ingredients which can exhibit phytotoxic effects at particular application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Preference is given to using alkyl naphthalenesulphonates, such as diisopropyl or diisobutyl naphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include especially ethylene oxide/propylene oxide block polymers, alkylphenol polyglycol ethers and tristryrylphenol polyglycol ethers, and the phosphated or sulphated derivatives thereof. Suitable anionic dispersants are especially lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate can be used with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which may be present in the seed dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz- und Schädlingsbekämpfungsmittel" [Chemistry of Crop Protection Agents and Pesticides], vol. 2, Springer Verlag, 1970, p. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, and beets, or else a wide variety of different vegetable seed. The seed dressing formulations usable in accordance with the invention, or the dilute preparations thereof, can also be used to dress seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the seed dressing procedure is to place the seed into a mixer, to add the particular desired amount of seed dressing formulations, either as such or after prior dilution with water, and to mix them until the formulation is distributed homogeneously on the seed. If appropriate, this is followed by a drying operation.

The application rate of the seed dressing formulations usable in accordance with the invention can be varied within a relatively wide range. It depends on the particular content of the active ingredient(s) in the formulations and on the seed. The application rates of active ingredients or active ingredient combinations are generally between 0.001 and 50 g per kilogram of seed, preferably between 0.01 and 15 g per kilogram of seed.

The inventive active ingredients are not just active against plant pests, hygiene pests and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp. (*Ctenocephalides canis*, *Ctenocephalides felis*), *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis*, *Periplaneta americana*, *Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The inventive active ingredients of the formula (I) are also suitable for controlling arthropods which attack agricultural livestock, for example cattle, sheep, goats, horses, pigs, donkeys, camels, buffaloes, rabbits, chickens, turkeys, ducks, geese, honey-bees, other domestic animals, for example dogs, cats, caged birds, aquarium fish, and experimental animals, for example hamsters, guinea pigs, rats and mice. The control of these arthropods is intended to reduce or prevent cases of deaths and reductions in performance (in the case of meat, milk, wool, hides, eggs, honey and the like), such that more economical and simpler animal keeping is possible through the use of the inventive active ingredients.

The application of the inventive active ingredients in the veterinary sector and in animal husbandry is accomplished in a known manner by enteral administration in the form of, for example, tablets, capsules, potions, drenches, granules, pastes, boluses, the feed-through method and suppositories, by parenteral administration, for example by injections (intramuscular, subcutaneous, intravenous, intraperitoneal and the like), implants, by nasal administration, by dermal use in the form, for example, of dipping or bathing, spraying, pouring-on and spotting-on, washing and powdering, and also with the aid of active ingredient-containing molded articles, such as collars, ear marks, tail marks, limb bands, halters, marking devices and the like.

When used for livestock, poultry, domestic animals and the like, the active ingredients of the formula (I) can be used as formulations (for example powders, emulsions, flowables) comprising the active ingredients in an amount of 1 to 80% by weight, either directly or after 100 to 10 000-fold dilution, or they may be used as a chemical bath.

It has also been found that the inventive compounds have strong insecticidal action against insects which destroy industrial materials.

Preferred but nonlimiting examples include the following insects:

beetles, such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *heterobostrychus brunneus*, *Sinoxylon* spec. *Dinoderus minutus*;

dermapterans, such as *Sirex juvencus*, *Urocerus gigas*, *Urocerus gigas taignus*, *Urocerus augur*;

termites, such as *Kalotermes flavicollis*, *Cryptotermes brevis*, *Heterotermes indicola*, *Reticulitermes flavipes*, *Reticu-*

*litermes santonensis, Reticulitermes lucifugus, Mastotermes darwiniensis, Zootermopsis nevadensis, Coptotermes formosanus;*
bristletails, such as *Lepisma saccharina*.

Industrial materials in the present connection are understood to mean inanimate materials, such as preferably plastics, adhesives, sizes, papers and cards, leather, wood, processed wood products and coating compositions.

The ready-to-use compositions may optionally also comprise other insecticides, and optionally one or more fungicides.

With respect to possible additional partners for mixing, reference is made to the insecticides and fungicides mentioned above.

At the same time, the inventive compounds can be used for protection of objects which come into contact with saltwater or brackish water, especially hulls, screens, nets, buildings, moorings and signalling systems, against fouling.

In addition, the inventive compounds can be used as antifouling compositions, alone or in combinations with other active ingredients.

The active ingredients are also suitable for controlling animal pests in the domestic sector, in the hygiene sector and in the protection of stored products, especially insects, arachnids and mites, which are found in enclosed spaces, for example homes, factory halls, offices, vehicle cabins and the like. They can be used to control these pests alone or in combination with other active ingredients and auxiliaries in domestic insecticide products. They are effective against sensitive and resistant species, and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium*, Opiliones *phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of domestic insecticides, they are used alone or in combination with other suitable active ingredients, such as phosphoric esters, carbamates, pyrethroids, neonicotinoids, growth regulators or active ingredients from other known classes of insecticides.

They are employed in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free or passive evaporation systems, moth papers, moth bags and moth gels, as granules or dusts, in baits for spreading or in bait stations.

Illustration of the Processes and Intermediates

The preparation and use examples which follow illustrate the invention without limiting it. The products were characterized by 1H NMR spectroscopy and/or LC/MS (liquid chromatography mass spectrometry).

The log P values were determined in accordance with OECD Guideline 117 (EC Directive 92/69/EEC) by HPLC (high-performance liquid chromatography) using reversed-phase (RP) columns (C18), by the following methods:

[a] The LC-MS determination in the acidic range is effected at pH 2.7 with 0.1% aqueous formic acid and acetonitrile (contains 0.1% formic acid) as eluents; linear gradient from 10% acetonitrile to 95% acetonitrile.

[b] The LC-MS determination in the neutral range is effected at pH 7.8 with 0.001 molar aqueous ammonium hydrogencarbonate solution and acetonitrile as eluents; linear gradient from 10% acetonitrile to 95% acetonitrile.

Calibration is effected with unbranched alkan-2-ones (having 3 to 16 carbon atoms) with known log P values (log P values determined on the basis of the retention times by linear interpolation between two successive alkanones).

The NMR spectra were determined with a Bruker Avance 400 fitted with a flow probe head (volume 60 µl). In individual cases, the NMR spectra were measured with a Bruker Avance II 1600.

The NMR data for selected examples are listed in conventional form (δ values, multiplet splitting, number of hydrogen atoms). The splitting of the signals was described as follows: s (singlet), d (doublet), t (triplet), q (quartet), quint (quintuplet), m (multiplet), b (for broad signals). Solvents used were CD₃CN, CDCl₃ or D6-DMSO, and tetramethylsilane (0.00 ppm) was used as reference.

Synthesis of Compounds of the Formula (Ia) by Process A

Example 1

5-Ethyl-1-(pyridin-3-yl)-1,5-dihydro-4H-pyrazolo[3,4-d]pyrimidin-4-one (6)

Step 1: 5-Amino-N-ethyl-1-(pyridin-3-yl)-1H-pyrazole-4-carboxamide (IIa-1-1)

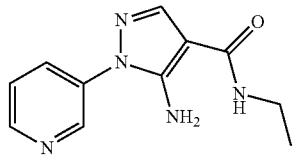 [SMILES: CCNC(=O)c1cnn(-c2cccnc2)c1N]

1.50 g (6.46 mmol) of ethyl 5-amino-1-(pyridin-3-yl)-1H-pyrazole-4-carboxylate were initially charged in 10 ml of ethanol and 15 ml of water, and 1.03 g (25.84 mmol) of sodium hydroxide were added. The reaction mixture was stirred at room temperature overnight and then at 40° C. for 2 h. The reaction mixture was then concentrated almost to dryness. The residue was slurried in a little water, and the insoluble fraction was filtered off with suction and dried well under reduced pressure. The sodium 5-amino-1-(pyridin-3-yl)-1H-pyrazole-4-carboxylate thus obtained was converted further directly.

1H NMR (D6-DMSO, 400 MHz) δ ppm: 8.87 (d, 1H), 8.50 (dd, 1H), 8.04-8.01 (m, 1H), 7.53-7.50 (m, 2H), 6.41 (bs, 2H)

150 mg (0.66 mmol, purity assumed to be 100%) of sodium 5-amino-1-(pyridin-3-yl)-1H-pyrazole-4-carboxylate were initially charged in 10 ml of N,N-dimethylformamide. To this were added 826 mg (2.98 mmol) of 4-(4,6-dimethoxy-1,3,5-triazin-2-yl)-4-methylmorpholinium chloride (DMT.MM) and 1.33 ml (2.65 mmol) of a 2 M ethylamine solution in tetrahydrofuran. The reaction mixture was stirred at bath temperature 50° C. overnight and then concentrated. The residue was taken up in acetonitrile and the insoluble portion was filtered off. The filtrate was concentrated and the residue was purified by means of MPLC using an RP(C-18) column with acetonitrile/water/ 0.1% formic acid. This gave 89 mg (94% pure, 55% of theory) of the title compound.

log P[a]: 0.50; log P[b]: 0.56; 1H NMR (D6-DMSO, 400 MHz) δ ppm: 8.80 (d, 1H), 8.58 (dd, 1H), 8.02-7.97 (m, 2H), 7.91 (bt, 1H), 7.56 (dd, 1H), 6.51 (bs, 2H), 3.29-3.19 (m, 2H), 1.10 (t, 3H)

Step 2: 5-Ethyl-1-(pyridin-3-yl)-1,5-dihydro-4H-pyrazolo[3,4-d]pyrimidin-4-one (6)

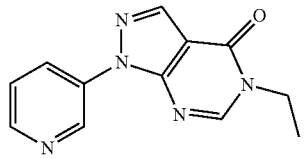 [SMILES: CCn1cnc2c(cnn2-c2cccnc2)c1=O]

60 mg (0.26 mmol) of 5-amino-N-ethyl-1-(pyridin-3-yl)-1H-pyrazole-4-carboxamide were initially charged in 0.40 ml of N,N-dimethylacetamide. 22 mg (0.13 mmol) of p-toluenesulphonic acid and 58 mg (0.39 mmol) of triethyl orthoformate were added thereto and the reaction mixture was heated to 120° C. in a CEM Discover microwave at 200 watts for 1 h. After checking the reaction by means of LC/MS, 0.05 ml of triethyl orthoformate was added and the mixture was stirred in the microwave at 120° C. for 15 minutes. After cooling, the reaction mixture was concentrated and the residue was purified by means of MPLC using an RP(C-18) column with acetonitrile/water. This gave 25 mg (100% pure, 39% of theory) of the title compound.

log P[a]: 0.98; log P[b]: 1.15; 1H NMR (D6-DMSO, 400 MHz) δ ppm: 9.27 (d, 1H), 8.63-8.60 (m, 2H), 8.45-8.42 (m, 2H), 7.64 (dd, 1H), 4.06 (q, 2H), 1.29 (t, 3H)

Example 2

5-Methyl-1-(pyrimidin-5-yl)-1,5-dihydro-4H-pyrazolo[3,4-d]pyrimidin-4-one (8)

Step 1: 5-Amino-N-methyl-1-(pyrimidin-5-yl)-1H-pyrazole-4-carboxamide (IIb-2-1)

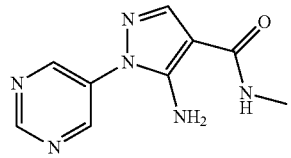 [SMILES: CNC(=O)c1cnn(-c2cncnc2)c1N]

To 1.00 g (4.29 mmol) of ethyl 5-amino-1-(pyrimidin-5-yl)-1H-pyrazole-4-carboxylate in 30 ml of ethanol were added 17 ml (17.2 mmol) of 1N sodium hydroxide solution. The reaction mixture was stirred at room temperature overnight and then concentrated. The residue was stirred in a little water. The insoluble fraction was filtered off with suction and dried well under reduced pressure. The sodium 5-amino-1-(pyrimidin-3-yl)-1H-pyrazole-4-carboxylate thus obtained was converted further directly.

1H NMR (D6-DMSO, 400 MHz) δ ppm: 9.10 (s, 2H), 8.33 (s, 1H), 7.56 (s, 1H), 6.57 (bs, 2H)

To 129 mg (0.53 mmol, purity assumed to be 100%) of sodium 5-amino-1-(pyrimidin-5-yl)-1H-pyrazole-4-carboxylate in 3 ml of N,N-dimethylformamide were added 187 mg (0.58 mmol) of (benzotriazol-1-yloxy)bisdimethylaminomethylium fluoroborate (TBTU). The resulting suspension was stirred at room temperature for 10 min. To the solution were added 0.29 ml (0.58 mmol) of a 2M methanamine solution in tetrahydrofuran and 0.14 ml (0.79 mmol) of N,N-diisopropylethylamine. The reaction mixture was stirred at room temperature overnight and then concentrated. The residue was purified by means of MPLC using an RP(C-18) column with acetonitrile/water/0.05% ammonium formate. This gave 22 mg (97% pure, 18% of theory) of the title compound.

log P[a]: 0.18; log P[b]: −0.01; 1H NMR (D6-DMSO, 400 MHz) δ ppm: 9.19 (s, 1H), 9.06 (s, 2H), 7.99 (s, 1H), 7.95-7.91 (m, 1H), 6.66 (bs, 2H), 2.72 (d, 3H)

Step 2: 5-Methyl-1-(pyrimidin-5-yl)-1,5-dihydro-4H-pyrazolo[3,4-d]pyrimidin-4-one (8)

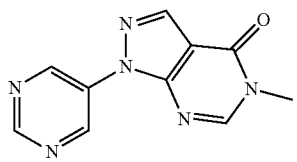 [SMILES: Cn1cnc2c(cnn2-c2cncnc2)c1=O]

55 mg (0.25 mmol) of 5-amino-N-methyl-1-(pyrimidin-5-yl)-1H-pyrazole-4-carboxamide were initially charged in 1 ml of N,N-dimethylacetamide. 22 mg (0.13 mmol) of p-toluenesulphonic acid and 84 µl (0.50 mmol) of triethyl orthoformate were added thereto and the reaction mixture was heated to 140° C. at 200 watts in a CEM Discover microwave for 1 h. After checking the reaction by means of LC/MS, 85 µl of triethyl orthoformate were added and the reaction mixture was stirred at 140° C. for a further 60 min. After cooling, the reaction mixture was concentrated and the residue was purified by means of MPLC using an RP(C-18) column with acetonitrile/water. This gave 16 mg (95% pure, 26% of theory) of the title compound.

log P[a]: 0.55; log P[b]: 0.55; 1H NMR (D6-DMSO, 400 MHz) δ ppm: 9.23 (s, 1H), 8.61 (s, 1H), 8.52 (s, 1H), 7.47 (d, 1H), 7.11 (d, 1H), 3.54 (s, 3H)

Example 3

5-Isopropyl-2-(pyridin-3-yl)-2,5-dihydro-4H-pyrazolo[3,4-d]pyrimidin-4-one (15)

Step 1: 3-Amino-N-isopropyl-1-(pyridin-3-yl)-1H-pyrazole-4-carboxamide (IIb-1-2)

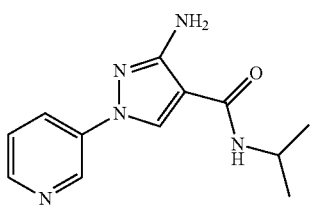 [SMILES: CC(C)NC(=O)c1cn(-c2cccnc2)nc1N]

To 5.50 ml (64.6 mmol) of isopropylamine in 250 ml of 1,2-dichloroethane were slowly added dropwise 32 ml of a 2M trimethylaluminium solution in toluene, and the mixture was stirred at room temperature for 1 h. 5.00 g (21.5 mmol) of ethyl 3-amino-1-(pyridin-3-yl)-1H-pyrazole-4-carboxylate were added thereto in portions and the reaction mixture was subsequently heated under reflux for 4 h. After cooling, the reaction mixture was cautiously expressed with argon into a 10% potassium sodium tartrate solution (about 600 ml). Some heat evolved in the course of this. The mixture was extracted by shaking three times with methylene chloride, and the organic phase was removed, dried over sodium sulphate, filtered and concentrated. The residue was stirred with a little acetonitrile to give a suspension. The insoluble portion was filtered off with suction and dried under reduced pressure. This gave 2.41 g (99% pure, 45% of theory) of the title compound.

log P[a]: 0.82; log P[b]: 1.05; 1H NMR (D6-DMSO, 400 MHz) δ ppm: 8.88 (d, 1H), 8.82 (s, 1H), 8.44 (dd, 1H), 7.99-7.96 (m, 1H), 7.69 (bd, 1H), 7.51 (dd, 1H), 5.81 (s, 2H), 4.06-4.01 (m, 1H), 1.15 (d, 6H)

As an alternative, it was possible to prepare the title compound as follows:

To 3.20 g (13.8 mmol) of ethyl 3-amino-1-(pyridin-3-yl)-1H-pyrazole-4-carboxylate in 38 ml of ethanol were added 55 ml (55.1 mmol) of a 1N sodium hydroxide solution. The reaction mixture was stirred at room temperature overnight and then concentrated. The residue was stirred in a little water. The insoluble fraction was filtered off with suction and dried well under reduced pressure. The sodium 3-amino-1-(pyridin-3-yl)-1H-pyrazole-4-carboxylate thus obtained was converted further directly.

1H NMR (D6-DMSO, 400 MHz) δ ppm: 8.95 (d, 1H), 8.32 (s, 2H), 8.06-8.03 (m, 1H), 7.40 (dd, 1H)

To 1.44 g (6.37 mmol, purity assumed to be 100%) of sodium 3-amino-1-(pyridin-3-yl)-1H-pyrazole-4-carboxylate in 15 ml of N,N-dimethylformamide were added 2.25 mg (7.00 mmol) of (benzotriazol-1-yloxy)bisdimethylaminomethylium fluoroborate (TBTU), and the resulting suspension was stirred at room temperature for 10 min. To the solution were added 2.17 ml (25.5 mmol) of isopropylamine and 1.66 ml (9.55 mmol) of N,N-diisopropylethylamine. The reaction mixture was stirred at room temperature overnight and then concentrated. The residue was purified by means of MPLC using an RP(C-18) column with acetonitrile/water/0.1% ammonium formate. This gave 732 mg (92% pure, 43% of theory) of the title compound.

Step 2: 5-Isopropyl-2-(pyridin-3-yl)-2,5-dihydro-4H-pyrazolo[3,4-d]pyrimidin-4-one (15)

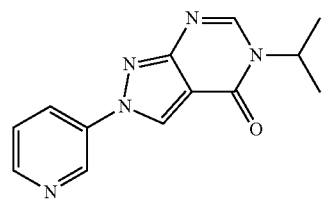 [SMILES: CC(C)n1cnc2nn(-c3cccnc3)cc2c1=O]

To 800 mg (3.26 mmol) of 3-amino-N-isopropyl-1-(pyridin-3-yl)-1H-pyrazole-4-carboxamide in 15 ml of N,N-dimethylacetamide were added 281 mg (1.63 mmol) of p-toluenesulphonic acid and 967 mg (6.52 mmol) of triethyl orthoformate. The reaction mixture was heated to 130° C. at 200 watts in a CEM Discover microwave for 1 h. After cooling, the precipitated solids were filtered off with suction, washed with a little acetonitrile and dried under reduced pressure. This gave 400 mg (99% pure, 48% of theory) of the title compound.

log P[a]: 1.06; log P[b]: 1.12; 1H NMR (D6-DMSO, 400 MHz) δ ppm: 9.47 (s, 1H), 9.27 (d, 1H), 8.66 (d, 1H), 8.46-8.42 (m, 2H), 7.64 (dd, 1H), 5.00 (quint, 1H), 1.42 (d, 6H)

Example 4

5-Ethyl-2-(pyridin-3-yl)-2,5-dihydro-4H-pyrazolo[3,4-d]pyrimidin-4-one (16)

Step 1: 3-Amino-N-ethyl-1-(pyridin-3-yl)-1H-pyrazole-4-carboxamide (IIb-1-1)

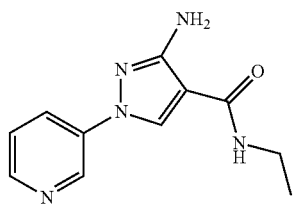 [SMILES: CCNC(=O)c1cn(-c2cccnc2)nc1N]

To 400 mg (1.77 mmol, purity assumed to be 100%) of sodium 3-amino-1-(pyridin-3-yl)-1H-pyrazole-4-carboxylate in 10 ml of N,N-dimethylformamide were added 625 mg (1.95 mmol) of (benzotriazol-1-yloxy)bisdimethylaminomethylium fluoroborate (TBTU), and the resulting suspension was stirred at room temperature for 10 min. To the yellowish solution were added 0.97 ml (1.95 mmol) of a 2M ethylamine solution in tetrahydrofuran and 0.46 ml (2.65 mmol) of N,N-diisopropylethylamine. The reaction mixture was stirred at room temperature overnight and then concentrated. The residue was purified by means of MPLC using an RP(C-18) column with acetonitrile/water/0.05% ammonium formate. This gave 234 mg (99% pure, 57% of theory) of the title compound.

log P[a]: 0.45; log P[b]: 0.77; 1H NMR (D6-DMSO, 400 MHz) δ ppm: 8.88 (d, 1H), 8.76 (s, 1H), 8.44 (dd, 1H), 7.98-7.92 (m, 2H), 7.52 (dd, 1H), 5.80 (bs, 2H), 3.32-3.21 (m, 2H), 1.12 (t, 3H)

Step 2: 5-Ethyl-2-(pyridin-3-yl)-2,5-dihydro-4H-pyrazolo[3,4-d]pyrimidin-4-one (16)

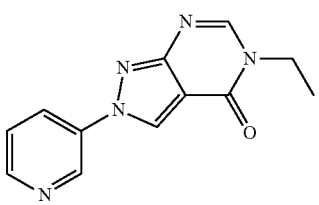 [SMILES: CCn1cnc2nn(-c3cccnc3)cc2c1=O]

To 234 mg (1.01 mmol) of 3-amino-N-ethyl-1-(pyridin-3-yl)-1H-pyrazole-4-carboxamide in 5 ml of N,N-dimethylacetamide were added 87 mg (0.51 mmol) of p-toluenesulphonic acid and 300 mg (2.02 mmol) of triethyl orthoformate. The reaction mixture was heated to 140° C. at 200 watts in a CEM Discover microwave for 1 h. After cooling, the reaction mixture was concentrated and taken up in a little water, and the solids were filtered off with suction and dried under reduced pressure. This gave 198 mg (99% pure, 80% of theory) of the title compound.

log P[a]: 0.70; log P[b]: 0.84; 1H NMR (D6-DMSO, 400 MHz) δ ppm: 9.47 (s, 1H), 9.26 (d, 1H), 8.65 (dd, 1H), 8.43 (dd, 1H), 8.39 (s, 1H), 7.64 (dd, 1H), 3.98 (q, 2H), 1.27 (t, 3H)

Example 5

5-Ethyl-6-methyl-2-(pyridin-3-yl)-2,5-dihydro-4H-pyrazolo[3,4-d]pyrimidin-4-one (29)

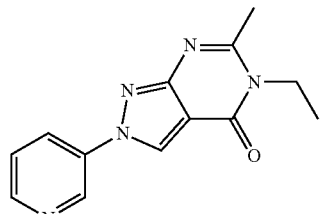

To 40 mg (0.17 mmol) of 3-amino-N-ethyl-1-(pyridin-3-yl)-1H-pyrazole-4-carboxamide in 2 ml of N,N-dimethylacetamide were added 15 mg (0.09 mmol) of p-toluenesulphonic acid and 56 mg (0.35 mmol) of triethyl orthoacetate. The reaction mixture was heated to 140° C. at 200 watts in a CEM Discover microwave for 2 h. Subsequently, the mixture was stirred at 130° C. for another 1 h. After cooling, the reaction mixture was concentrated and the residue was purified by means of MPLC using an RP(C-18) column with acetonitrile/water. The fraction isolated therefrom was purified once again by means of preparative HPLC with acetonitrile/water. It was possible to isolate 6 mg (100% pure, 14% of theory) of the title compound.

log P[a]: 0.93; log P[b]: 1.03; 1H NMR (D6-DMSO, 400 MHz) δ ppm: 9.40 (s, 1H), 9.25 (bs, 1H), 8.64 (bd, 1H), 8.40 (m, 1H), 7.63 (dd, 1H), 4.06 (q, 2H), 2.62 (s, 3H), 1.24 (t, 3H)

Example 6

5-Ethyl-2-(pyridin-3-yl)-6-(trifluoromethyl)-2,5-dihydro-4H-pyrazolo[3,4-d]pyrimidin-4-one (32)

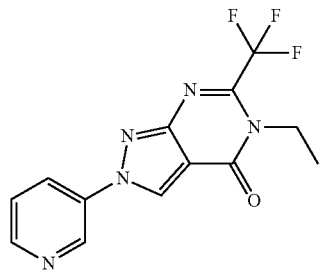 [SMILES: CCn1c(C(F)(F)F)nc2nn(-c3cccnc3)cc2c1=O]

To 50 mg (0.22 mmol) of 3-amino-N-ethyl-1-(pyridin-3-yl)-1H-pyrazole-4-carboxamide and 90 μl (0.65 mmol) of triethylamine in 10 ml of acetonitrile were slowly added, at 0° C., 52 μl (0.37 mmol) of trifluoroacetic anhydride. Subsequently, the mixture was stirred at 0° C. for 2 h and then at 50° C. for 12 h. After adding 52 μl of trifluoroacetic anhydride and 90 μl of triethylamine, the mixture was heated under reflux overnight. After cooling, the reaction mixture was concentrated and the residue was purified by means of MPLC using an RP(C-18) column with acetonitrile/water. This gave 44 mg (95% pure, 62% of theory) of the title compound.

log P[a]: 2.07; log P[b]: 2.06; 1H NMR (D6-DMSO, 400 MHz) δ ppm: 9.63 (s, 1H), 9.29 (d, 1H), 8.69 (bd, 1H), 8.45 (m, 1H), 7.67 (dd, 1H), 4.10 (q, 2H), 1.29 (t, 3H)

Example 7

3-Isopropyl-6-(3-pyridyl)pyrazolo[3,4-d]triazin-4-one (36)

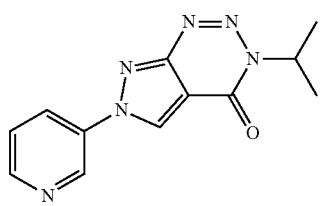 [SMILES: CC(C)n1nnc2nn(-c3cccnc3)cc2c1=O]

To 100 mg (0.41 mmol) of 3-amino-N-isopropyl-1-(pyridin-3-yl)-1H-pyrazole-4-carboxamide in 2.5 ml of water and 2.5 ml of concentrated hydrochloric acid were added 239 mg (3.47 mmol) of sodium nitrite in 2.5 ml of water. The reaction mixture was stirred at 70° C. overnight. After cooling, the reaction mixture was discharged onto water and the pH of the solution was adjusted to 7 with saturated sodium bicarbonate solution. The mixture was extracted by shaking three times with methylene chloride, and the organic phases were combined, dried over magnesium sulphate, filtered and concentrated. The residue was applied to RP(C-18) material and purified by means of MPLC using an RP(C-18) cartridge with water/acetonitrile/0.1% formic acid eluent. This gave 6 mg (100% pure, 6% of theory) of the title compound.

log P[a]: 1.72; log P[b]: 1.70; 1H NMR (D6-DMSO, 400 MHz) δ ppm: 9.71 (s, 1H), 9.33 (d, 1H), 8.74 (dd, 1H), 8.53-8.50 (m, 1H), 7.72-7.69 (m, 1H), 5.31 (quint, 1H), 1.49 (d, 6H)

Example 8

5-Isopropyl-2-pyridazin-4-yl-pyrazolo[3,4-d]pyrimidin-4-one (38)

Step 1: 3-Amino-N-isopropyl-1-pyridazin-4-yl-pyrazole-4-carboxamide (IIb-3-1)

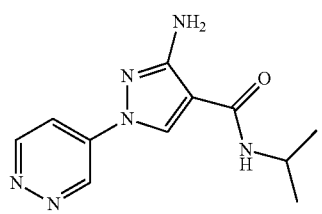 [SMILES: CC(C)NC(=O)c1cn(-c2ccnnc2)nc1N]

To 0.55 ml (6.43 mmol) of isopropylamine in 2.5 ml of 1,2-dichloroethane were slowly added dropwise 3.22 ml of a 2M trimethylaluminium solution in toluene, and the mixture was stirred at room temperature for 30 minutes. 500 mg (2.14 mmol) of ethyl 3-amino-1-pyridazin-4-ylpyrazole-4-carboxylate were added thereto in portions and the reaction mixture was subsequently heated under reflux overnight. After cooling, the reaction mixture was cautiously expressed with argon into a 10% potassium sodium tartrate solution (about 100 ml). The mixture was extracted by shaking three times with methylene chloride, and the organic phase was removed, dried over sodium sulphate, filtered and concentrated. The residue was applied to RP(C-18) material and purified by means of MPLC using an RP(C-18) cartridge with water/acetonitrile/0.1% formic acid eluent. This gave 100 mg (88% pure, 17% of theory) of the title compound.

log P[a]: 0.74; log P[b]: 0.74; 1H NMR (D6-DMSO, 400 MHz) δ ppm: 9.50 (d, 1H), 9.19 (d, 1H), 9.00 (s, 1H), 7.84 (bd, 1H), 7.71-7.69 (m, 1H), 6.04 (s, 2H), 4.06-4.01 (m, 1H), 1.17-1.15 (d, 6H)

Step 2: 5-Isopropyl-2-pyridazin-4-yl-pyrazolo[3,4-d]pyrimidin-4-one (38)

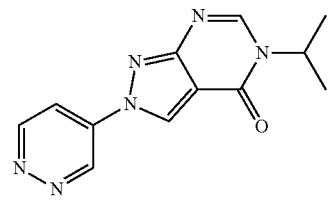 [SMILES: CC(C)n1cnc2nn(-c3ccnnc3)cc2c1=O]

To 100 mg (0.41 mmol) of 3-amino-N-isopropyl-1-pyridazin-4-ylpyrazole-4-carboxamide in 3 ml of N,N-dimethylacetamide were added 35 mg (0.20 mmol) of p-toluenesulphonic acid and 120 mg (0.81 mmol) of triethyl orthoformate. The reaction mixture was heated to 140° C. at 200 watts in a CEM Discover microwave for 1 h. After cooling, the reaction mixture was concentrated, taken up in a little saturated sodium bicarbonate solution and extracted three times with methylene chloride. The organic phases were separated, combined, dried over sodium sulphate, filtered and concentrated. The residue was stirred in acetonitrile, applied to RP(C-18) material and purified by means of MPLC using an RP(C-18) cartridge with water/acetonitrile/0.1% formic acid eluent. This gave 8 mg (77% pure, 6% of theory) of the title compound.

log P[a]: 0.85; log P[b]: 0.85

Synthesis of Aminopyrazoles of the Formulae (IIIa) and (IIIb)

Ethyl 5-amino-1-(pyridin-3-yl)-1H-pyrazole-4-carboxylate (IIIa-1) and ethyl 3-amino-1-(pyridin-3-yl)-1H-pyrazole-4-carboxylate (IIIb-1) by process B

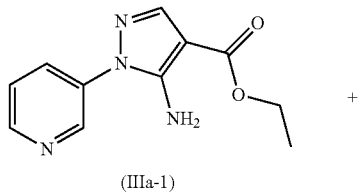

(IIIa-1)

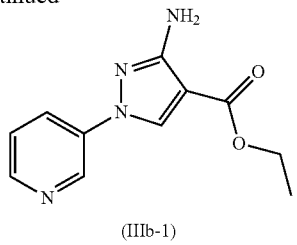

82.3 g (0.59 mol) of potassium carbonate were initially charged in a three-neck flask. The flask was baked out under argon and the following were added in succession: 2.70 g (0.014 mol) of copper(I) iodide, 44.0 g (0.28 mol) of ethyl 3-amino-4-pyrazolecarboxylate and 440 ml of N,N-dimethylacetamide. The suspension was stirred for 10 minutes and then 7.18 g (0.056 mol) of trans-1,2-diaminocyclohexane and 53.77 g (0.34 mol) of 3-bromopyridine were added. The reaction mixture was brought to reflux temperature and stirred at 145° C. overnight. After cooling, the reaction mixture was filtered off with suction, the mother liquor was concentrated and the residue was purified by means of MPLC using an RP(C-18) column with acetonitrile/water/0.1% formic acid. A first fraction contained 39 g of a mixture of 70% ethyl 5-amino-1-(pyridin-3-yl)-1H-pyrazole-4-carboxylate (IIIa-1) and 30% ethyl 3-amino-1-(pyridin-3-yl)-1H-pyrazole-4-carboxylate (IIIb-1), according to LC/MS. A second fraction contained 10 g, consisting of 83% ethyl 3-amino-1-(pyridin-3-yl)-1H-pyrazole-4-carboxylate (IIIb-1) according to LC/MS. A separation of (IIIa-1) and (IIIb-1) from the first fraction by means of preparative HPLC gave a further 24.5 g (96% purity) of ethyl 5-amino-1-(pyridin-3-yl)-1H-pyrazole-4-carboxylate as the formate (IIIa-1) and 11.5 g (99% purity) of ethyl 3-amino-1-(pyridin-3-yl)-1H-pyrazole-4-carboxylate (IIIb-1).

(IIIa-1). HCOOH log P[a]: 1.18; log P[b]: 1.27; 1H NMR (D6-DMSO, 400 MHz) δ ppm: 12.8 (bs, 1H), 8.78 (d, 1H), 8.62 (dd, H), 8.14 (s, 1H), 7.99-7.96 (m, 1H), 7.76 (s, 1H), 7.58 (dd, H), 6.51 (bs, 2H), 4.23 (q, 2H), 1.28 (t, 3H)

(IIIb-1) log P[a]: 1.12; log P[b]: 1.32; 1H NMR (D6-DMSO, 400 MHz) δ ppm: 9.06 (d, 1H), 8.86 (s, 1H), 8.47 (d, 1H), 8.19 (bd, 1H), 7.49 (dd, 1H), 5.78 (bs, 2H), 4.26 (q, 2H), 1.30 (t, 3H)

Ethyl 5-amino-1-(pyridin-3-yl)-1H-pyrazole-4-carboxylate (IIIa-1) by process C

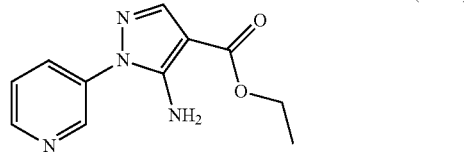

To 500 mg (3.43 mmol) of 3-hydrazinopyridine hydrochloride (1:1) in 5 ml of ethanol were added 581 mg (3.43 mmol) of ethyl 2-cyano-3-ethoxyacrylate. The reaction mixture was heated under reflux for 2 h and cooled, and 0.48 ml (3.43 mmol) of triethylamine was added. Subsequently, the mixture was concentrated, and the residue was taken up in a little water, acidified slightly and extracted repeatedly with dichloromethane. The organic phases were combined, dried over sodium sulphate and concentrated. The residue was purified by means of MPLC using a silica gel column with cyclohexane/ethyl acetate. This gave 179 mg (98% pure, 22% of theory) of the title compound. (IIIa-1) log P[a]: 1.10; 1H NMR (D6-DMSO, 400 MHz) δ ppm: 8.78 (d, 1H), 8.62 (dd, 1H), 7.99-7.96 (m, 1H), 7.76 (s, 1H), 7.58 (dd, 1H), 6.49 (bs, 2H), 4.23 (q, 2H), 1.28 (t, 3H); 13C NMR (D6-DMSO 150 MHz) δ ppm: 163.6, 150.6, 148.6, 145.0, 141.2, 134.9, 131.7, 124.5, 95.1, 59.3, 14.7

Ethyl 3-amino-1-(pyridin-3-yl)-1H-pyrazole-4-carboxylate (IIIb-1) by process D

Step 1: Benzaldehyde pyridin-3-yl hydrazone (VII-1)

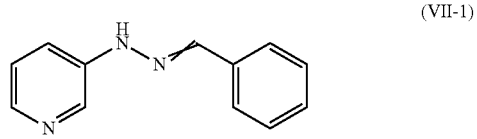 [SMILES: C(=NNc1cccnc1)c1ccccc1]

To 15.00 g (103.0 mol) of 3-hydrazinopyridine hydrochloride (1:1) and 9.49 g (68.7 mmol) of potassium carbonate in 150 ml of toluene were slowly added 7 ml (68.7 mmol) of benzaldehyde dissolved in 100 ml of toluene. The reaction mixture was stirred under reflux (with a water separator) overnight. After cooling, the insoluble fractions were filtered off with suction. The solid residue was stirred repeatedly in ethyl acetate. The solids were filtered off with suction and stirred repeatedly in hot isopropanol. The insoluble fractions were filtered off with suction and discarded; the filtrate was concentrated. The 5.50 g (98% pure, 40% of theory) of the title compound were converted further directly.

log P[a]: 0.86; log P[b]: 2.22

Step 2: Ethyl 3-[2-benzylidene-1-(pyridin-3-yl)hydrazino]-2-cyanoacrylate (VIII-1)

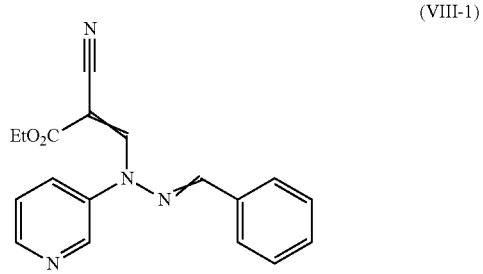 [SMILES: CCOC(=O)C(C#N)=CN(N=Cc1ccccc1)c1cccnc1]

To 5.50 g (27.9 mmol) of 3-benzaldehyde pyridin-3-yl hydrazone in 14 ml of toluene were added 4.72 g (27.9 mmol) of ethyl 2-cyano-3-ethoxyacrylate. The reaction mixture was heated under reflux first for 2 h and, after addition of a spatula-tip of para-toluenesulphonic acid, for a further 2 h. After cooling, the precipitated solids were filtered off with suction and the organic phase was discarded. The solids were initially charged once again in 15 ml of toluene and admixed with 1.69 g (10.0 mmol) of ethyl 2-cyano-3-ethoxyacrylate. The reaction mixture was heated under reflux overnight, left to stand until it had cooled, and then diluted with toluene. After addition of a little (about 0.5 ml) acetonitrile, the insoluble residue was filtered off with suction and dried under reduced pressure. 3.11 g (90% pure, 31% of theory) of the title compound were isolated.

log P[a]: 2.54; log P[b]: 2.48

Step 3: Ethyl 3-amino-1-(pyridin-3-yl)-1H-pyrazole-4-carboxylate (IIIb-1)

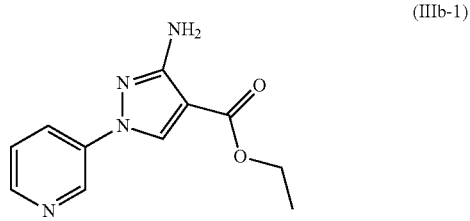 [SMILES: CCOC(=O)c1cn(-c2cccnc2)nc1N]

3.00 g (9.37 mmol) of ethyl 3-[2-benzylidene-1-(pyridin-3-yl)hydrazino]-2-cyanoacrylate were initially charged in 11 ml of ethanol, and 1.1 ml (13.11 mmol) of a 37% hydrochloric acid solution were added. The reaction mixture was heated under reflux for 1 h, cooled and then concentrated. The residue was stirred twice in lukewarm toluene. The solids were filtered off with suction and dried under reduced pressure. 2.64 g (92% pure, 97% of theory) of the title compound were isolated.

Ethyl 5-amino-1-(pyrimidin-5-yl)-1H-pyrazole-4-carboxylate (IIIa-2) and ethyl 3-amino-1-(pyrimidin-5-yl)-1H-pyrazole-4-carboxylate (IIIb-2) by process B

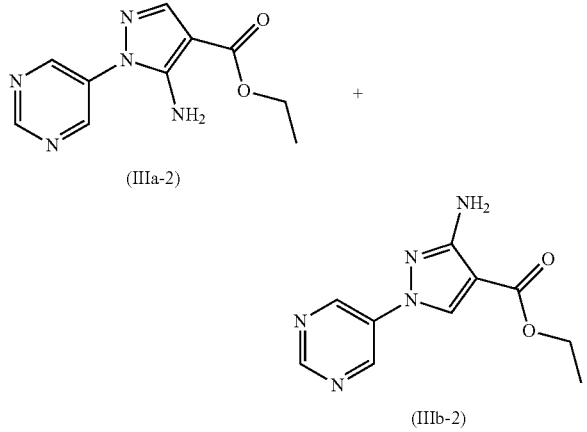

9.35 g (67.6 mmol) of potassium carbonate were initially charged in a three-neck flask. The flask was baked out under argon and the following were added in succession: 0.31 g (1.61 mmol) of copper(I) iodide, 5.00 g (32.2 mmol) of ethyl 3-amino-4-pyrazolecarboxylate and 50 ml of N,N-dimethylacetamide. The suspension was stirred for 10 minutes, then 0.77 ml (6.45 mmol) of trans-1,2-diaminocyclohexane and 6.15 g (39.7 mmol) of 5-bromopyrimidine were added. The reaction mixture was brought to reflux temperature and stirred at about 150° C. for a total of 7.5 h. After cooling, the reaction mixture was concentrated and the residue was purified by means of MPLC using an RP(C-18) column with acetonitrile/water. The fraction isolated contained 2.97 g of a mixture of 90% ethyl 5-amino-1-(pyrimidin-5-yl)-H-pyrazole-4-carboxylate (IIIa-2) and 9% ethyl 3-amino-1-(pyrimidin-5-yl)-1H-pyrazole-4-carboxylate (IIIb-2) according to LC/MS. The products were subsequently separated by means of preparative HPLC. Two fractions were isolated: 0.99 g (100% purity) of ethyl 5-amino-1-(pyrimidin-5-yl)-1H-pyrazole-4-carboxylate (IIIa-2) and 0.42 g (95% purity) of ethyl 3-amino-1-(pyrimidin-5-yl)-1H-pyrazole-4-carboxylate (IIIb-2) (IIIa-2) log P[a]: 1.16; log P[b]: 1.12; 1H NMR (D6-DMSO, 400 MHz) δ ppm: 9.23 (s, 1H), 9.04 (s, 2H), 7.81 (s, 1H), 6.97 (bs, 2H), 4.23 (q, 2H), 1.28 (t, 3H); 13C NMR (D6-DMSO 150 MHz) δ ppm: 163.4, 156.9, 152.2, 151.1, 142.0, 133.7, 95.2, 59.3, 14.7

(IIIb-2) log P[a]: 1.12; log P[b]: 1.08; 1H NMR (D6-DMSO, 400 MHz) δ ppm: 9.24 (s, 1H), 9.07 (s, 1H), 8.96 (s, 1H), 5.89 (bs, 2H), 4.27 (q, 2H), 1.30 (t, 3H)

Ethyl 5-amino-1-pyridazin-4-yl-pyrazole-4-carboxylate (IIIa-3) and ethyl 3-amino-1-pyridazin-4-yl-pyrazole-4-carboxylate (IIIb-3) by process B

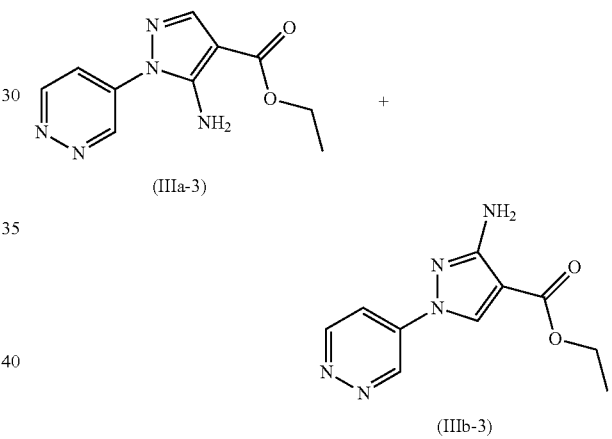

9.35 g (67.7 mmol) of potassium carbonate were initially charged in a three-neck flask. The flask was baked out under argon and the following were added in succession: 0.31 g (1.61 mmol) of copper(I) iodide, 5.00 g (32.2 mmol) of ethyl 3-amino-4-pyrazolecarboxylate and 100 ml of N,N-dimethylacetamide. The suspension was stirred for 10 minutes, then 0.86 ml (6.45 mmol) of trans-1,2-diaminocyclohexane and 6.15 g (38.7 mmol) of 4-bromopyridazine were added. The reaction mixture was brought to reflux temperature and stirred at about 150° C. for a total of 7.5 h. After cooling, the reaction mixture was filtered, the filtrate was concentrated and the residue was purified by means of MPLC using an RP(C-18) column with water/acetonitrile/0.1% formic acid. The fractions containing a relatively high content were taken up in acetonitrile for the purpose of another separation, leaving behind an insoluble portion. The latter was filtered off with suction and dried. This gave 1.18 g (80% pure, 13% of theory) of ethyl 3-amino-1-pyridazin-4-yl-pyrazole-4-carboxylate (IIIb-3).

The filtrate was applied to RP(C-18) material and purified by means of MPLC using an RP(C-18) column with water/acetonitrile/0.1% formic acid. The isolated fraction contained 0.41 g of a mixture of 73% ethyl 5-amino-1- pyridazin-4-yl-pyrazole-4-carboxylate (IIIa-3) and 13% ethyl 3-amino-1-pyridazin-4-yl-pyrazole-4-carboxylate (IIIb-3) according to LC/MS.

(IIIa-3) log P[a]: 1.12; log P[b]: 1.12

(IIIb-3) log P[a]: 0.90; log P[b]: 0.94; 1H NMR (D6-DMSO, 400 MHz) δ ppm: 9.75 (bs, 1H), 9.22 (bs, 1H), 9.13 (s, 1H), 7.99-7.96 (m, 1H), 6.00 (s, 2H), 4.28 (q, 2H), 1.31 (t, 3H)

Further compounds of the formulae (Ia) and (Ib) are listed in the tables below.

TABLE 1

Compounds of the formula (Ia)

| Ex. No. | Het | Q | V | R$^1$ | R$^2$ |
|---|---|---|---|---|---|
| 1 | pyridin-3-yl | CH | O | CH(CH$_3$)$_2$ | H |
| 2 | pyridin-3-yl | CH | O | phenyl | H |
| 3 | pyridin-3-yl | CH | O | CH$_2$CF$_3$ | H |
| 4 | pyridin-3-yl | CH | O | 4-chlorophenyl | H |
| 5 | pyridin-3-yl | CH | O | pyrimidin-2-ylmethyl | H |
| 6 | pyridin-3-yl | CH | O | C$_2$H$_5$ | H |
| 7 | pyridin-3-yl | CH | O | CH$_3$ | H |
| 8 | pyrimidin-5-yl | CH | O | CH$_3$ | H |

TABLE 2

Compounds of the formula (Ib)

| Ex. No. | Het | Q | V | R$^1$ | R$^2$ |
|---|---|---|---|---|---|
| 9 | pyridin-3-yl | CH | O | C$_2$H$_5$ | H |
| 10 | pyridin-3-yl | CH | O | phenyl | H |
| 11 | phenyl | CH | O | pyrimidin-2-ylmethyl | H |
| 12 | pyridin-3-yl | CH | O | CH$_2$CF$_3$ | H |

TABLE 2-continued

Compounds of the formula (Ib)

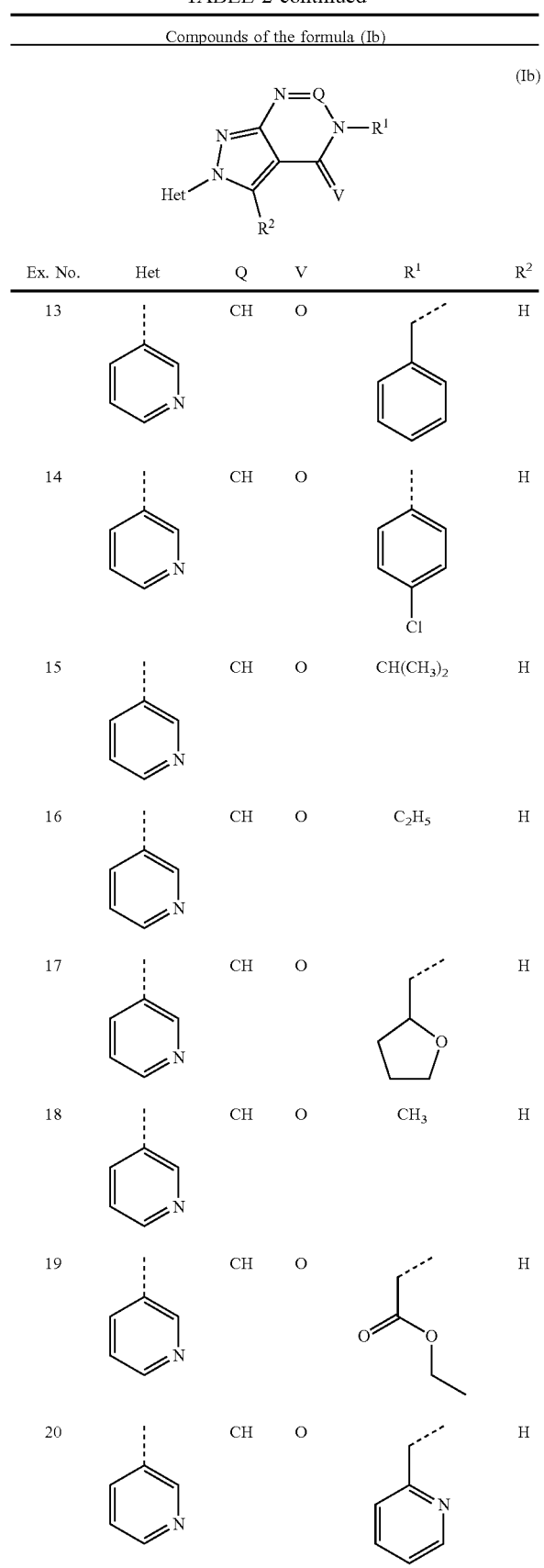

| Ex. No. | Het | Q | V | R¹ | R² |
|---|---|---|---|---|---|
| 13 | 3-pyridyl | CH | O | benzyl | H |
| 14 | 3-pyridyl | CH | O | 4-Cl-phenyl | H |
| 15 | 3-pyridyl | CH | O | $CH(CH_3)_2$ | H |
| 16 | 3-pyridyl | CH | O | $C_2H_5$ | H |
| 17 | 3-pyridyl | CH | O | tetrahydrofuran-2-ylmethyl | H |
| 18 | 3-pyridyl | CH | O | $CH_3$ | H |
| 19 | 3-pyridyl | CH | O | $CH_2C(O)OC_2H_5$ | H |
| 20 | 3-pyridyl | CH | O | 2-pyridylmethyl | H |

TABLE 2-continued

Compounds of the formula (Ib)

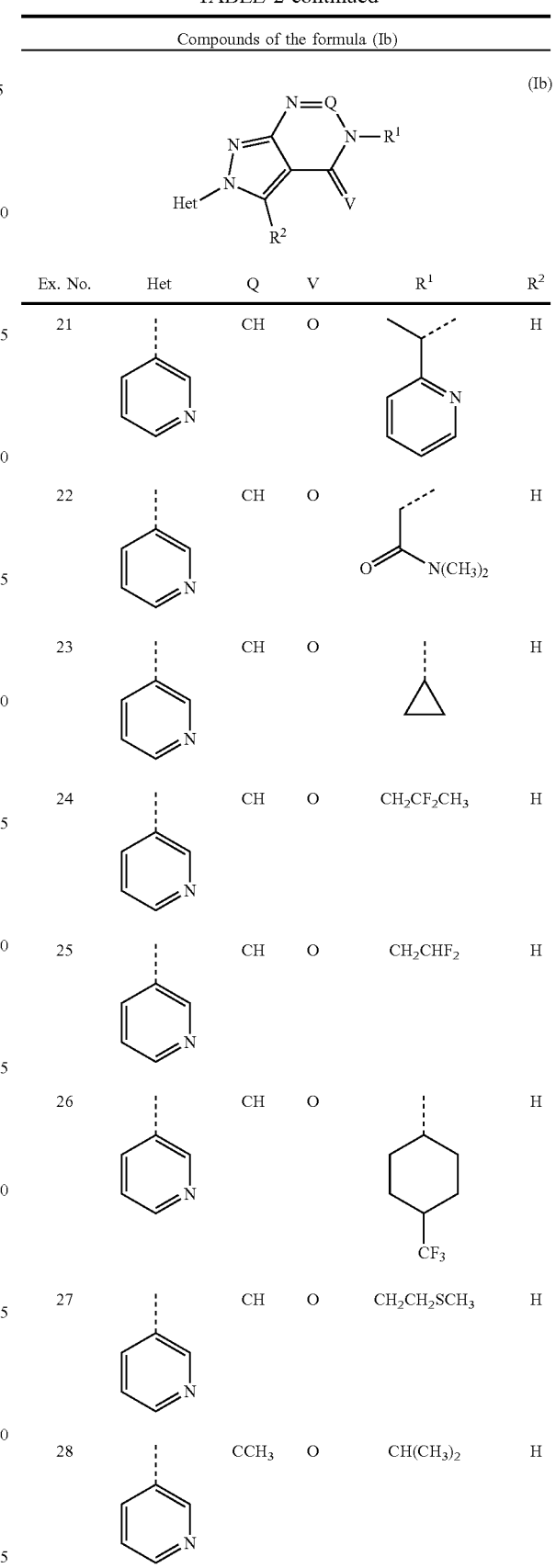

| Ex. No. | Het | Q | V | R¹ | R² |
|---|---|---|---|---|---|
| 21 | 3-pyridyl | CH | O | 2-pyridyl(CH) | H |
| 22 | 3-pyridyl | CH | O | $CH_2C(O)N(CH_3)_2$ | H |
| 23 | 3-pyridyl | CH | O | cyclopropyl | H |
| 24 | 3-pyridyl | CH | O | $CH_2CF_2CH_3$ | H |
| 25 | 3-pyridyl | CH | O | $CH_2CHF_2$ | H |
| 26 | 3-pyridyl | CH | O | 4-$CF_3$-cyclohexyl | H |
| 27 | 3-pyridyl | CH | O | $CH_2CH_2SCH_3$ | H |
| 28 | 3-pyridyl | $CCH_3$ | O | $CH(CH_3)_2$ | H |

TABLE 2-continued

Compounds of the formula (Ib)

(Ib)

| Ex. No. | Het | Q | V | R¹ | R² |
|---|---|---|---|---|---|
| 29 | 3-pyridyl | CCH₃ | O | C₂H₅ | H |
| 30 | 3-pyridyl | CH | O | 1-cyanocyclopropyl | H |
| 31 | 3-pyridyl | CH | O | CHCH₃CH₂SCH₃ | H |
| 32 | 3-pyridyl | CCF₃ | O | C₂H₅ | H |
| 33 | 3-pyridyl | CH | O | CH₂CH(CH₂)₂ | H |
| 34 | 3-pyridyl | CH | O | CH₂C(CH₃)₃ | H |
| 35 | 3-pyridyl | CH | O | CH₂C(CH₃)₂ | H |
| 36 | 3-pyridyl | CH | N | CH(CH₃)₂ | H |
| 37 | 5-pyrimidyl | CH | O | CH(CH₃)₂ | H |
| 38 | 4-pyridazinyl | CH | O | CH(CH₃)₂ | H |
| 39 | 3-pyridyl | CH | O | 4-tolyl | H |

TABLE 3

Analytical data for the compounds reported

| Ex. No. | logP[a] | logP[b] | 1H NMR (D6-DMSO, 400 MHz) σ (ppm) |
|---|---|---|---|
| 1 | 1.31 | | |
| 2 | 1.57 | | |
| 3 | 1.48 | | |
| 4 | 2.04 | | |
| 5 | 0.80 | 0.91 | |
| 6 | 0.98 | 1.15 | |
| 7 | 0.58 | 0.82 | 9.27 (d, 1H), 8.62 (d, 1H), 8.60 (s, 1H), 8.46-8.43 (m, 2H), 7.64 (dd, 1H), 3.53 (s, 3H) |
| 8 | 0.55 | 0.55 | |
| 9 | 0.80 | | |
| 10 | 1.40 | | |
| 11 | 0.63 | | |
| 12 | 1.27 | | |
| 13 | 1.59 | | |

TABLE 3-continued

Analytical data for the compounds reported

| Ex. No. | logP[a] | logP[b] | 1H NMR (D6-DMSO, 400 MHz) σ (ppm) |
|---|---|---|---|
| 14 | 1.74 | | |
| 15 | 1.06 | 1.12 | |
| 16 | 0.70 | 0.84 | |
| 17 | 1.07 | 1.12 | 9.47 (s, 1H), 9.26 (d, 1H), 8.65 (dd, 1H), 8.44-8.41 (m, 1H), 8.27 (s, 1H), 7.63 (dd, 1H), 4.15-4.07 (m, 2H), 3.92-3.86 (m, 1H), 3.83-3.77 (m, 1H), 3.68-3.63 (m, 1H), 2.02-1.78 (m, 3H), 1.63-1.54 (m, 1H) |
| 18 | 0.45 | 0.52 | 9.48 (s, 1H), 9.27 (d, 1H), 8.65 (dd, 1H), 8.43 (dd, 1H), 8.35 (s, 1H), 7.63 (dd, 1H), 3.46 (s, 3H) |
| 19 | 0.98 | 1.09 | 9.51 (s, 1H), 9.27 (d, 1H), 8.66 (dd, 1H), 8.43 (dd, 1H), 8.35 (s, 1H), 7.64 (dd, 1H), 4.80 (s, 2H), 4.18 (q, 2H), 1.22 (t, 3H) |
| 20 | 0.76 | 1.06 | 9.45 (s, 1H), 9.26 (d, 1H), 8.66 (dd, 1H), 8.48-8.47 (m, 2H), 8.44-8.41 (dd, 1H), 7.80 (dt, 1H), 7.64 (dd, 1H), 7.40 (bd, 1H), 7.30 (dd, 1H), 5.29 (s, 2H) |
| 21 | 1.13 | 1.32 | 9.45 (s, 1H), 9.26 (d, 1H), 8.65 (dd, 1H), 8.53 (bd, 1H), 8.46 (s, 1H), 8.42 (bd, 1H), 7.82 (dt, 1H), 7.63 (dd, 1H), 7.49 (d, 1H), 7.32 (dd, 1H), 6.12 (q, 1H), 1.85 (d, 3H) |
| 22 | 0.47 | 0.51 | 9.49 (s, 1H), 9.27 (d, 1H), 8.65 (dd, 1H), 8.43 (dt, 1H), 8.19 (s, 1H), 7.64 (dd, 1H), 4.89 (s, 2H), 3.09 (s, 3H), 2.88 (s, 3H) |
| 23 | 0.79 | 0.83 | 9.47 (s, 1H), 9.26 (d, 1H), 8.64 (dd, 1H), 8.42 (dt, 1H), 8.27 (s, 1H), 7.63 (dd, 1H), 3.16 (quint, 1H), 1.06-0.90 (m, 4H) |
| 24 | 1.19 | 1.21 | 9.52 (s, 1H), 9.26 (d, 1H), 8.66 (dd, 1H), 8.44 (dt, 1H), 8.28 (s, 1H), 7.64 (dd, 1H), 4.53 (t, 2H), 1.71 (t, 3H) |
| 25 | 0.91 | 0.96 | 9.53 (s, 1H), 9.27 (d, 1H), 8.66 (d, 1H), 8.43 (bd, 1H), 8.35 (s, 1H), 7.64 (dd, 1H), 6.37 (tt, 1H), 4.47 (dt, 2H) |
| 26 | 2.08 | 2.06 | 9.50 (s, 1H), 9.27 (d, 1H), 8.65 (bd, 1H), 8.44-8.42 (m, 2H), 7.63 (dd, 1H), 4.70-4.63 (m, 1H), 3.81-3.75 (m, 1H), 2.04-1.90 (m, 6H), 1.56-1.46 (m, 2H) |
| 27 | 1.13 | 1.19 | 9.47 (s, 1H), 9.26 (d, 1H), 8.65 (dd, 1H), 8.43 (dt, 1H), 8.38 (s, 1H), 7.64 (dd, 1H), 4.14 (t, 2H), 2.83 (t, 2H), 2.12 (s, 3H) |
| 28 | 1.28 | 1.35 | 9.33 (s, 1H), 9.24 (d, 1H), 8.63 (d, 1H), 8.38 (bd, 1H), 7.60 (dd, 1H), 4.78-4.55 (m, 1H), 2.65 (s, 3H), 1.55 (d, 6H) |
| 29 | 0.93 | 1.03 | |
| 30 | 0.82 | 0.85 | |
| 31 | 1.36 | 1.40 | 9.45 (s, 1H), 9.26 (d, 1H), 8.65 (dd, 1H), 8.44-8.41 (m, 2H), 7.64 (dd, 1H), 5.05-4.94 (m, 1H), 3.07-2.94 (m, 2H), 2.04 (s, 3H), 1.50 (d, 3H) |
| 32 | 2.07 | 2.06 | |
| 33 | 1.23 | 1.27 | 9.48 (s, 1H), 9.27 (d, 1H), 8.65 (dd, 1H), 8.42-8.41 (m, 2H), 7.65-7.62 (m, 1H), 3.82 (d, 2H), 1.28-1.20 (m, 1H), 0.53-0.48 (m, 2H), 0.44-0.41 (m, 2H) |
| 34 | 1.70 | 1.71 | 9.46 (s, 1H), 9.26 (d, 1H), 8.65 (dd, 1H), 8.44-8.40 (m, 1H), 8.29 (s, 1H), 7.65-7.62 (m, 1H), 3.85 (s, 2H), 0.94 (s, 9H) |
| 35 | 1.42 | 1.44 | 9.47 (s, 1H), 9.26 (d, 1H), 8.65 (dd, 1H), 8.44-8.41 (m, 1H), 8.34 (s, 1H), 7.65-7.62 (m, 1H), 3.78 (d, 2H), 2.10-2.03 (m, 1H), 0.89 (d, 6H) |
| 36 | 1.72 | 1.70 | 9.71 (s, 1H), 9.33 (d, 1H), 8.74 (dd, 1H), 8.53-8.50 (m, 1H), 7.72-7.69 (m, 1H), 5.31 (quint, 1H), 1.49 (d, 6H) |
| 37 | 0.93 | 0.92 | 9.53 (s, 1H), 9.47 (s, 2H), 9.27 (d, 1H), 8.48 (s, 1H), 4.99 (q, 1H), 1.42 (bd, 6H) |
| 38 | 0.85 | 0.85 | |
| 39 | 1.73 | 1.73 | 9.56 (s, 1H), 9.29 (d, 1H), 8.67 (dd, 1H), 8.47-8.44 (m, 1H), 8.30 (s, 1H), 7.67-7.64 (m, 1H), 7.40-7.35 (m, 4H), 2.40 (s, 3H) |

BIOLOGICAL EXAMPLES

*Myzus persicae*—Spray Test

Solvent: 78 parts by weight of acetone 1.5 parts by weight of dimethylformamide

Emulsifier: alkylaryl polyglycol ether

To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (*Brassica pekinensis*) infested by all stages of the green peach aphid (*Myzus persicae*) are sprayed with an active ingredient formulation of the desired concentration.

After 6 days, the effect in % is determined. 100% means that all the aphids have been killed; 0% means that no aphids have been killed.

In this test, for example, the following compounds from the preparation examples showed an efficacy of 100% at an application rate of 500 g/ha: 3, 9, 11, 12, 15, 16, 17, 18, 19, 23, 24, 25, 30, 33, 34, 37, 39

In this test, for example, the following compounds from the preparation examples showed an efficacy of 90% at an application rate of 500 g/ha: 2, 4, 5, 10, 14, 20, 21, 22, 26, 28, 29, 36, 38

In this test, for example, the following compounds from the preparation examples showed an efficacy of 100% at an application rate of 100 g/ha: 35

Myzus persicae—Spray Test
Solvent: 7 parts by weight of dimethylformamide
Emulsifier: alkylaryl polyglycol ether To produce an appropriate active ingredient formulation, 1 part by weight of active ingredient is dissolved using the specified parts by weight of solvent and made up with water containing an emulsifier concentration of 1000 ppm until the desired concentration is attained. To produce further test concentrations, the preparation is diluted with emulsifier-containing water. If the addition of ammonium salts or/and penetrants is required, these are each added in a concentration of 1000 ppm to the formulation solution.

Bell pepper plants (Capsicum annuum) heavily infested by the green peach aphid (Myzus persicae) are treated by spraying to runoff point with the active ingredient formulation in the desired concentration.

After 6 days, the kill in % is determined. 100% means that all the aphids have been killed; 0% means that no aphids have been killed.

In this test, for example, the following compounds from the preparation examples showed an efficacy of 95% at an application rate of 20 ppm: 31

In this test, for example, the following compounds from the preparation examples showed an efficacy of 90% at an application rate of 20 ppm: 27

Meloidogyne incognita Test (MELGIN)
Solvent: 125.0 parts by weight of acetone

To produce an appropriate active ingredient formulation, 1 part by weight of active ingredient is mixed with the specified amounts of solvent and the concentrate is diluted to the desired concentration with water.

Vessels are filled with sand, active ingredient solution, an egg/larvae suspension of the southern root-knot nematode (Meloidogyne incognita) and lettuce seeds. The lettuce seeds germinate and the plants develop. The galls develop on the roots After 14 days, the nematicidal efficacy in % is determined by the formation of galls. 100% means that no galls have been found; 0% means that the number of galls on the treated plants corresponds to the untreated control.

In this test, for example, the following compound from the preparation examples showed an efficacy of 100% at an application rate of 20 ppm: 14

The invention claimed is:
1. A compound of formula (Ib)

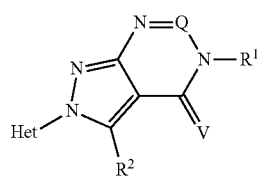

(Ib)

in which
Het is a radical from the group of

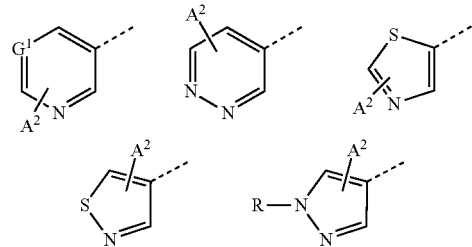

in which the dotted line represents the bond to the nitrogen atom in the pyrazole ring and $G^1$ is N or C-$A^1$, $A^1$ is hydrogen, halogen, cyano, nitro, alkyl, haloalkyl, alkoxy, haloalkoxy or in each case optionally substituted cycloalkyl or cycloalkenyl, $A^2$ is hydrogen, halogen, cyano, nitro, alkyl, haloalkyl, alkoxy, haloalkoxy or in each case optionally substituted cycloalkyl or cycloalkenyl, R is hydrogen, alkyl, haloalkyl or optionally substituted cycloalkyl, $R^1$ is a radical from the group of alkyl, haloalkyl, cyanoalkyl, alkenyl, haloalkenyl, alkynyl, haloalkynyl, alkoxy, haloalkoxy, optionally halogen-substituted alkoxyalkyl, optionally halogen-substituted bis(alkoxy)alkyl, optionally halogen-substituted alkylthioalkyl, optionally halogen-substituted alkylcarbonylalkyl, optionally halogen-substituted alkylsulphinylalkyl, optionally halogen-substituted alkylsulphonylalkyl, dialkylaminosulphanylalkyl, dialkylaminosulphinylalkyl, dialkylaminosulphonylalkyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkyl, optionally halogen-, cyano-, nitro-, alkyl-, haloalkyl-, alkoxy-, haloalkoxy-, alkoxycarbonyl-, haloalkoxycarbonyl- or hetaryl-substituted (hetaryl itself optionally being substituted by alkyl or halogen) cycloalkylalkyl, optionally substituted heterocyclyl, optionally halogen-, cyano-, nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonyl amino-, alkoxyalkyl-, haloalkoxyalkyl-, alkenyl-, alkynyl-, cycloalkylalkyl-, alkylcarbonyl-, alkoxycarbonyl- or aminocarbonyl-substituted heterocyclylalkyl, optionally halogen-, cyano-, nitro-, alkyl-, haloalkyl-, cycloalkyl- (which is optionally substituted), alkoxy- or haloalkoxy-substituted aryl, optionally halogen-, cyano-, alkyl-, haloalkyl-, cycloalkyl- (which is optionally substituted), alkoxy- or haloalkoxy-substituted arylalkyl, optionally halogen-, cyano- nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetaryl, optionally halogen-, cyano- nitro-, alkyl-, haloalkyl-, cycloalkyl- (which is optionally substituted), alkoxy-, haloalkoxy-, alkylthio-, haloalkylthio-, alkylsulphinyl-, alkylsulphonyl-, haloalkylsulphinyl-, haloalkylsulphonyl-, amino-, alkylamino-, dialkylamino-, alkylcarbonylamino-, alkoxycarbonylamino-, alkoxyalkyl-, haloalkoxyalkyl-, alkenyl-, alkynyl-, cycloalkylalkyl-, alkylcarbonyl-, alkoxycarbonyl- or aminocarbonyl-substituted hetarylalkyl, $R^2$ is hydrogen or alkyl, Q is C—$R^3$ in which $R^3$ is a radical from the group of hydrogen, alkyl, haloalkyl, OH, alkoxy, haloalkoxy, SH, alkylsulphanyl, alkylsulphinyl, alkylsulphonyl, $NH_2$, alkylamino and dialkylamino, V is a radical from the group of oxygen, sulphur and $NR^4$ and $R^4$ is a radical from the group of hydrogen, cyano, alkyl, haloalkyl and cycloalkyl, with the proviso that compounds in which $R^1$ is phenyl or 4-chlorophenyl and, at the same time, Q is C, $R^3$ is methyl, V is O, $G^1$ is N or C-$A^1$ and $A^1$ and $A^2$ are each H are excluded.

2. A composition comprising a content of at least one compound of formula (Ib) according to claim 1 and one or more customary extenders and/or surfactants.

3. A method for controlling one or more pests comprising contacting the pests or their surroundings, habitat, and/or storage space thereof with a compound of formula (Ib) according to claim 1.

4. A compound of formula (Ib) according to claim 1, wherein

Het is

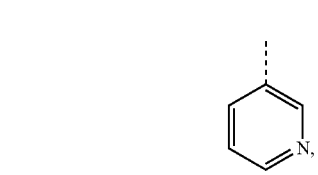

$R^1$ is $CH(CH_3)_2$,
$R^2$ is hydrogen,
Q is CH, and
V is oxygen.

5. A compound of formula (Ib) according to claim 1, wherein Het is

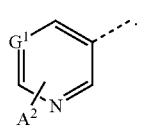

6. A compound of formula (Ib) according to claim 1, wherein Het is

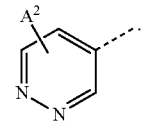

7. A compound of formula (Ib) according to claim 1, wherein Het is

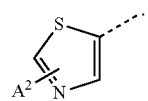

8. A compound of formula (Ib) according to claim 1, wherein Het is

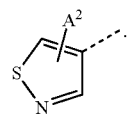

9. A compound of formula (Ib) according to claim 1, wherein Het is

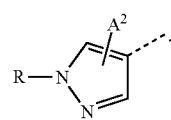

10. A compound of formula (Ib) according to claim 1, wherein V is oxygen.

11. A compound of formula (Ib) according to claim 1, wherein V is sulphur.

12. A compound of formula (Ib) according to claim 1, wherein V is $NR^4$.

13. A compound of formula (Ib) according to claim 5, wherein $G^1$ is N.

14. A compound of formula (Ib) according to claim 5, wherein $G^1$ is C-$A^1$.

* * * * *